United States Patent
Hübner et al.

(10) Patent No.: US 11,278,609 B2
(45) Date of Patent: Mar. 22, 2022

(54) **POLYPEPTIDES DERIVED FROM *ENTEROCOCCUS* AND THEIR USE FOR VACCINATION AND THE GENERATION OF THERAPEUTIC ANTIBODIES**

(71) Applicants: ALBERT-LUDWIGS-UNIVERSITÄT FREIBURG, Freiburg (DE); UNIVERSITE DE CAEN BASSE-NORMANDIE, Caen (FR)

(72) Inventors: Johannes Hübner, Freiburg (DE); Axel Hartke, Quistreham (FR); Luis Felipe Romero Saavedra, Munich (DE)

(73) Assignees: KLINIKUM DER UNIVERSITÄT MÜNCHEN, Munich (DE); UNIVERSITE DE CAEN BASSE-NORMANDIE, Caen (FR)

( * ) Notice: Subject to any disclaimer, the term of this patent is extended or adjusted under 35 U.S.C. 154(b) by 0 days.

(21) Appl. No.: 15/122,842

(22) PCT Filed: Feb. 25, 2015

(86) PCT No.: PCT/EP2015/053948
§ 371 (c)(1),
(2) Date: Aug. 31, 2016

(87) PCT Pub. No.: WO2015/132103
PCT Pub. Date: Sep. 11, 2015

(65) Prior Publication Data
US 2017/0087239 A1   Mar. 30, 2017

(30) Foreign Application Priority Data
Mar. 4, 2014   (EP) ..................... 14157628

(51) Int. Cl.
*A61K 39/09* (2006.01)
*C07K 14/24* (2006.01)
*C07K 16/12* (2006.01)
*A61K 39/02* (2006.01)
*A61K 39/00* (2006.01)

(52) U.S. Cl.
CPC ............ *A61K 39/09* (2013.01); *A61K 39/025* (2013.01); *C07K 14/24* (2013.01);
(Continued)

(58) Field of Classification Search
CPC .......... C07K 14/24; C12Q 1/68; C07H 21/00; C12N 1/00; C12N 5/00; C12N 15/00
(Continued)

(56) References Cited

U.S. PATENT DOCUMENTS

| | | | |
|---|---|---|---|
| 6,583,275 B1* | 6/2003 | Doucette-Stamm | ... C07K 14/24 435/243 |
| 2012/0121638 A1* | 5/2012 | Huebner | ............ A61K 39/025 424/190.1 |
| 2012/0315278 A1* | 12/2012 | Throsby et al. | ... C07K 16/1271 424/142.1 |

FOREIGN PATENT DOCUMENTS

| | | | |
|---|---|---|---|
| EP | 1477802 A1 | 11/2004 | |
| EP | 1028749 | * 6/2008 | ......... C07K 16/1275 |

(Continued)

OTHER PUBLICATIONS

Earl, A.M., et al., "Full=Penicillin-binding protein transpeptidase." XP002726914, retrieved from EBI accession No. UNIPROT: R3ZLV9.
(Continued)

*Primary Examiner* — Jana A Hines
(74) *Attorney, Agent, or Firm* — Saliwanchik, Lloyd & Eisenschenk

(57) ABSTRACT

Medicament for the treatment or the prevention of a bacterial infection, characterized in that it contains at least one polypeptide selected from the group of SEQ ID NO: 1 to SEQ ID NO: 9, and contiguous fragments thereof, wherein said at least one polypeptide or contiguous fragment thereof induces opsonic antibodies in a patient in need thereof. The polypeptides or the contiguous fragments thereof according
(Continued)

to the present invention can be used for the preparation of a vaccine against an infection against *Enterococcus*.

12 Claims, 3 Drawing Sheets

Specification includes a Sequence Listing.

(52) U.S. Cl.
CPC ...... *C07K 16/1228* (2013.01); *C07K 16/1267* (2013.01); *A61K 2039/572* (2013.01)

(58) Field of Classification Search
USPC ....... 435/243, 6, 325, 320.1; 536/24.3, 23.1, 536/32
See application file for complete search history.

(56) References Cited

FOREIGN PATENT DOCUMENTS

| EP | 2 248 533 A1 | 11/2010 | | |
|---|---|---|---|---|
| EP | 2248533 | * | 11/2010 | ............ A61K 39/02 |
| WO | WO2007016556 | * | 2/2007 | ............ A61K 47/48 |

OTHER PUBLICATIONS

Kropec, et al., "Identification of SagA as a novel vaccine target for the prevention of *Enterococcus faecium* infections." *Microbiology*, 2011, 157(12): 3429-3434.

Sadowy, E., et al., "High abundance and diversity of antimicrobial resistance determinants among early vancomycin-resistant *Enterococcus faecium* in Poland." *Eur J Clin Microbiol Infect Dis*, 2013, 32(9): 1193-1203.

Sava, I.G., et al., "Enterococcal surface protein contributes to persistence in the host but is not a target of opsonic and protective antibodies in *Enterococcus faecium* infection." *Journal of Medical Microbiology*, 2010, 59(9): 1001-1004.

Feldgarden, M., et al., "The Genome Sequence of *Enterococcus faecium* strain 1,231,408.," adhesion lipoprotein, Feb. 20, 2009, received from EBI accession No. GenBank: EEV57494.1, Database accession No. EEV57949. [retrieved from: https://www.ncbi.nlm.nih.gov/protein/EEV5749].

* cited by examiner

POLYPEPTIDES DERIVED FROM *ENTEROCOCCUS* AND THEIR USE FOR VACCINATION AND THE GENERATION OF THERAPEUTIC ANTIBODIES

CROSS REFERENCE TO A RELATED APPLICATION

This application is a National Stage Application of International Application Number PCT/EP2015/053948, filed Feb. 25, 2015; which claims priority to European Application No. 14157628.0, filed Mar. 4, 2014; which are incorporated herein by reference in their entirety.

The present invention relates to a medicament for the treatment or the prevention of a bacterial infection, characterized in that it contains at least one polypeptide selected from the group of SEQ ID NO: 1 to SEQ ID NO: 9, and contiguous fragments thereof, wherein said at least one polypeptide or contiguous fragment thereof induces opsonic antibodies in a patient in need thereof. The polypeptides or the contiguous fragments thereof according to the present invention can be used for the preparation of a vaccine against an infection against *Enterococcus*.

BACKGROUND OF THE PRESENT INVENTION

Enterococci are among the three most common nosocomial pathogens and due to their multiple antibiotic resistances cause substantial morbidity and mortality, especially among intensive care patients and the immunocompromised. While several new antibiotics have been introduced in the last decade, resistance against these new drugs is developing and spreading rapidly. Life-threatening systemic disease such as endocarditis caused by resistant strains may at times be untreatable. Therefore, alternative treatment and prevention strategies are desperately needed to counter the rise of multiply resistant clones in hospitals and nursing homes worldwide. A better understanding of the different enterococcal cell surface structures will help to target new therapeutic and prophylactic approaches.

It is known that all gram-positive bacteria (also those belonging to the genus of *Enterococcus*) contain in the cell wall several specific carbohydrates and proteins. In the course of the present invention several proteins have been identified that play a possible role in the dynamic equilibrium of the outer cell wall.

The humoral immune response is mediated by antibody molecules secreted by plasma cells. Antigen that binds to the B-cell antigen receptor signals B-cells and is at the same time internalized and processed into peptides that activate armed helper T-cells. Signals from the bound antigen and from the helper T-cell induce the B-cell to proliferate and differentiate into plasma cells secreting specific antibody. These antibodies protect the host from infection in three main ways. First, said antibodies can inhibit the toxic effects or infectivity of pathogens by binding to them. Such antibodies are termed neutralizing antibodies. Second, by coating the pathogens, said antibodies can enable accessory cells that recognize the Fc portions of arrays of antibodies to ingest and kill the pathogen. This process is called opsonisation. Third, antibodies can trigger the activation of the complement system. Complement proteins can strongly enhance opsonisation or can directly kill certain bacterial cells.

Genomics is a recently introduced new discipline that studies the functioning of an organism through its genome and has greatly accelerated the identification of new candidates for vaccine development. More than fifty genomic sequences of enterococci are currently available in different data bases and this number is constantly growing. The analysis of all these genes and genomes is an extremely fast and efficient approach to predict the cellular localization and/or function of proteins synthesized in an organism. This in silico approach combined with functional genomics data will in future years help to identify new targets for vaccination tests (Sette and Rappuoli, 2010).

EP2248533 discloses a medicament for the treatment or the prevention of a bacterial infection is disclosed which contains a polypeptide having a contiguous sequence of at least six amino acids of SEQ ID NO:1 as disclosed therein. Said polypeptide can be used for the preparation of a vaccine against an *Enterococcus* infection.

Similarly, EP2450053 discloses another polypeptide used for the preparation of a vaccine against an *Enterococcus* infection.

WO 2010/089340 relates to a protective peptide of *Enterococcus faecalis* (*E. faecalis*) or a functional active variant thereof, optionally further consisting of additional amino acid residue(s); a nucleic acid coding for the same; a pharmaceutical composition comprising said peptide or said nucleic acid; an antibody or functional active fragment thereof specifically binding to the antigen; a hybridoma cell line which produces said antibody; a method for producing said antibody; a pharmaceutical composition comprising said antibody; the use of said peptide or said nucleic acid for the manufacture of a medicament for the immunization or treatment of a subject; the use of said antibody or functional fragment thereof for the manufacture of a medicament for the treatment of an infection; a method of diagnosing an *E. faecalis* infection; and the use of said peptide for the isolation and/or purification and/or identification of an interaction partner of the peptide.

WO2007141278 relates to human binding molecules (e.g. antibodies) having killing activity against enterococci and uses thereof.

For the production of vaccines it is important that the antigen elicits antibodies which inhibit the pathogenic activity of the pathogenic microorganism. The opsonophagocytic assay has been used to simulate the immune response in vitro and to identify enterococcal virulence factors (see, for example, Romero-Steiner et al., Use of opsonophagocytosis for serological evaluation of pneumococcal vaccines. Clin Vaccine Immunol. 2006 February; 13(2):165-9). Protective antibodies elicited by a vaccine have therefore the effect of neutralization, opsonisation and complement activation whereby antibodies induced by a specific antigen may also have two or even three of the protective activities. However, only few antigens have been identified so far that may offer the potential of inducing a protective immune response, and therefore would be promising vaccine targets.

It is therefore an object of the present invention to provide new polypeptides or parts thereof which can be used in order to produce protective antibodies, preferably IgG antibodies against said polypeptide or parts of said polypeptide. It is furthermore an object of the present invention, to provide vaccine compositions against gram-positive bacteria, and in particular Enterococci, based on said polypeptides or parts thereof.

Fang Teng et al. (in: Fang Teng et al. An *Enterococcus faecium* Secreted Antigen, SagA, Exhibits Broad-Spectrum Binding to Extracellular Matrix Proteins and Appears Essential for *E. faecium* Growth, Infection and Immunity, September 2003, p. 5033-5041, Vol. 71, No. 9) discloses the extracellular and secreted E. faecium SagA protein as apparently essential for growth, showing broad-spectrum binding to ECM proteins, forming oligomers, and antigenic during infection. Furthermore, antibodies produced against recombinant Sag A are described. Although the protein is described as secreted antigen, there is no disclosure of an actual antigenicity of Sag A in vivo, let alone the formation of opsonic and/or protective antibodies in a host. The publication merely describes a C-terminal domain of Sag A that is "similar to that found in various proteins", including P60 (52% similarity) of L. monocytogenes, which has cell wall hydrolase activity, and has also been shown to be involved in virulence. The publication is thus limited to the functional characterization of Sag A.

Furthermore, the presence of a surface-exposed proteins does not automatically result in the formation of opsonic and/or protective antibodies in the host. In fact, to the knowledge of the inventors, only two protein antigens have been confirmed so far in E. faecalis as being the target of protective antibodies: an ABC transporter described by Burnie and colleagues (Burnie et al. Identification of ABC transporters in vancomycin-resistant Enterococcus faecium as potential targets for antibody therapy. FEMS Immunol Med Microbiol (2002) vol. 33 (3) pp. 179-89) and, only recently, the collagen adhesin ACE (Singh et al. Importance of the collagen adhesin ace in pathogenesis and protection against Enterococcus faecalis experimental endocarditis. PLoS Pathog (2010) vol. 6(1) pp. e1000716). Two other surface proteins have been shown to be not protective, namely the enterococcal aggregation substance (McCormick et al. Antibodies to a surface-exposed, N-terminal domain of aggregation substance are not protective in the rabbit model of Enterococcus faecalis infective endocarditis. Infect Immun (2001) vol. 69 (5) pp. 3305-14) and the enterococcal surface protein Esp (Sava et al., Sava I G Enterococcal surface protein contributes to persistence in the host but is not a target of opsonic and protective antibodies in Enterococcus faecium infection. J Med Microbiol. 2010 September; 59(Pt 9):1001-4). Studies on several other protein antigens have been reported in the literature as being involved in virulence, while no protective effect of either passive or active immunization has been documented. Therefore, to date, only very few vaccine targets, either proteinaceous or carbohydrates, have been identified in E. faecium.

In one aspect thereof, the object of the present invention is solved by providing a medicament for the treatment or the prevention of a bacterial infection, characterized in that said medicament contains at least one polypeptide selected from the group of SEQ ID NO: 1 to SEQ ID NO: 9, and contiguous fragments (active variants) thereof, wherein said at least one polypeptide or contiguous fragment thereof induces antibodies in a patient in need thereof. The present invention is based on the surprising finding that the polypeptides of SEQ ID NO: 1 to 9 or active fragments thereof can be used to provide such a vaccine target, and/or can form the basis to provide effective and preferably therapeutically effective (e.g. opsonic) antibodies.

In the context of the present invention, the inventors identified nine proteins (polypeptides) of E. faecium E155 and their homologues in E. faecalis, respectively, at least parts of which function as effective antigens (epitopes), and thus can be used to provide an active polypeptide and/or peptide-based vaccine or a passive antibody-based medicament for a prevention and/or treatment of a bacterial infection, such as, for example, infection caused by gram-positive bacteria, and in particular by Enterococci.

The main protective defense mechanism of the human immune system against enterococci is phagocytosis, which occurs through direct recognition of certain enterococcal surface structures or through opsonisation by antibody and complement. Therefore, in another aspect of the invention, the active vaccine according to the present invention can be administered to patients (preferably before the infection), in order to stimulate their immune response and to avoid an infection in a hospital or a nursing home.

The amino acid sequences of the polypeptides SEQ ID NOs: 1 to 9 are both disclosed in the attached Sequence Listing and Table 1 (see below). The polypeptides of SEQ ID NOs: 1 to 9 have been shown to be effective in opsonophagocytotic assays (see examples), a clear indication for their protective effect also in vivo.

TABLE 1

Polypeptides as identified according to the present invention.

| Protein name and abbreviation | SEQ ID No. | Locus Tag/Acc No. | Method for identification |
| --- | --- | --- | --- |
| low affinity penicillin-binding protein 5 (PBP5) | 1 | EFAU004_00870; AAD26697 | Biotin, High pH, Trypsin |
| Basic membrane lipoprotein (BML) | 2 | EFAU004_00080; YP_005353284 | Biotin, High pH, Trypsin |
| peptidoglycan-binding protein LysM (LysM) | 3 | EFAU004_01059; WP_002337891 | Biotin, High pH, Trypsin |
| D-alanyl-D-alanine carboxypeptidase (Dala) | 4 | EFAU004_01127; WP_016922432 | Biotin, High pH, Trypsin |
| PpiC-type peptidyl-prolylcis-trans isomerase (PpiC) | 5 | EFAU004_02526; WP_002291335 | Biotin, High pH, Trypsin |
| Enolase (Enol) | 6 | EFAU004_02073; YP_005355275 | Biotin, High pH, Trypsin |
| SCP-like extracellular protein (serine protease) (SCP) | 7 | WP_002353118.1 | Biotin, High pH, Trypsin |
| Adhesion lipoprotien (Adlip) | 8 | EFUG_02345; EEV57494 | Biotin, High pH, Transcriptomic data |
| Periplasmic solute binding family (PSB) | 9 | EFAU004_00598 | Biotin, High pH, Transcriptomic data |

The nine polypeptides according to the invention were overexpressed and purified in order to inject said proteins into a rabbit. The animal then produced antibodies, based on the combination of proteins. The different sera as obtained showed a significant opsonic killing activity, confirmed by the stimulation of an in vitro immune response by opsonophagocytic assay. Moreover, the protein Sag A is used as a positive control in all the experiments, a promising vaccine target in E. faecium (EP 2 248 533 B1).

The person skilled in the art is aware that not necessarily the whole polypeptide has to be used for the production of a vaccine. Even shorter fragments based on contiguous amino acids of a polypeptide can be used. Such fragments are designated herein as "active variants" and comprise an (at least one) "epitope" that usually consist of at least six contiguous amino acids out of the SEQ ID NO: 1 to 9. Preferably, however, said polypeptides have at least 10, more preferably at least 15 and more preferred at least 20 contiguous amino acids of the SEQ ID NO: 1 to 9. In a particularly preferred embodiment, the polypeptide has at least 30, more preferred at least 50 and especially preferred at least 100 contiguous amino acids of SEQ ID NO: 1 to 9. Preferred fragments are disclosed in table 2 and SEQ ID Nos. 10 to 167.

Active variants may also be obtained by changing the sequence of the polypeptide as defined herein and are characterized by having a biological activity similar to that displayed by the protective peptide of the sequence of SEQ ID NOs: 1 to 9 from which the variant is derived, including the ability to induce protective immune responses and/or to show protection against *E. faecium* or *E. faecalis* e.g. in an animal model as disclosed herein, wherein any variant may be tested as described in the Examples. In another preferred embodiment of the invention the polypeptide of the invention or an active variant, can consist of 1 to 400 additional amino acid residue(s), preferably 1 to 350, 1 to 300, 1 to 250, 1 to 200, 1 to 150, more preferably 1 to 100, even more preferably at most 1 to 50, most preferably 1, 2, 3, 4, 5, 10, 20, 30 or 40 additional amino acids residue(s).

In one preferred embodiment of the invention, the peptide and/or the antigens of the invention comprising additional amino acid residue(s) as defined herein is characterized in that it comprises at least 2, preferably at least 3, more preferably at least 4 epitopes as defined above. The antigenic peptide and/or the epitope may be flanked by the amino acid residue(s) C-terminally, N-terminally or C- and N-terminally.

The active variant of the polypeptide may have added at least one additional amino acid residue heterologous or homologous to the peptide of any of the SEQ ID NOs: 1 to 9. Homologous refers to any amino acid residue which is identical to the amino acid residue of the protein from *E. faecium* or *E. faecalis* from which the peptide is derived, wherein the peptide of any of the SEQ ID NO: 1 to 9 is derived from the polypeptide as listed in Table 1. Alternatively or additionally, the polypeptide may consist of the antigen, optionally the additional sequence as defined above and at least one amino acid residue heterologous to the antigen, preferably a marker protein.

The active variant of the polypeptide may be obtained by sequence alterations in the peptide, wherein the peptide with the sequence alterations retains a function of the unaltered peptide, e.g. having a biological activity similar to that displayed by the unaltered peptide. Such sequence alterations can include, but are not limited to, (conservative) amino acid substitutions, deletions, mutations and insertions. The additional sequence or amino acid residue(s) as defined above consists of (an) amino acid residue(s), which may be any amino acid, which may be either an L- and/or a D-amino acid, naturally occurring and otherwise. Preferably the amino acid is any naturally occurring amino acid such as alanine, cysteine, aspartic acid, glutamic acid, phenylalanine, glycine, histidine, isoleucine, lysine, leucine, methionine, asparagine, proline, glutamine, arginine, serine, threonine, valine, tryptophan or tyrosine. However, the amino acid may also be a modified or unusual amino acid. Examples of those are 2-aminoadipic acid, 3-aminoadipic acid, beta-alanine, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4-di aminobutyric acid, desmosine, 2,2'-di-aminopimelic acid, 2,3-diaminopropionic acid, N-ethylglycine, N-ethylasparagine, hydroxylysine, allo-hydroxylysine, 3-hydroxyproloine, 4-hydroxyproloine, isodesmosine, allo-isoleucine, N-methylglycine, N-methylisoleucine, 6-N-Methyllysine, N-methylvaline, norvaline, norleucine or ornithine. Additionally, the amino acid may be subject to modifications such as posttranslational modifications. Examples of modifications include acetylation, amidation, blocking, formylation, γ-carboxyglutamic acid hydroxylation, glycosylation, methylation, phosphorylation and sulfatation. If more than one additional or heterologous amino acid residue is present in the peptide, the amino acid residues may be the same or different from one another.

Alternatively, the polypeptide of any of the SEQ ID NOs: 1 to 9 may be essentially identical to or even consists of the antigen, i.e. the full-length protein is used as the epitope and/or antigen.

The person skilled in the art is aware that with suitable computer programs the hydrophobicity and hydrophilicity of the areas of the polypeptide can be determined.

Therefore, the preferred fragments are mainly hydrophilic since the parts of the polypeptide which are located on the outer areas of the folded polypeptide are preferred for the preparation of a vaccine. Moreover, when longer parts of the polypeptide are used, it is more likely that not only linear epitopes are within the fragment but also conformational epitopes are present which occur in the course of three-dimensional folding of the polyprotein.

Preferred active peptides (active variants)—and thus epitopes—according to the present invention are listed in the following table 2, and are disclosed in SEQ ID Nos. 10 to 167.

TABLE 2

Preferred peptides (epitopes) according to the present invention

| Polypeptide/ SEQ ID No./ Reference Acc No./size of polypeptide | Position/sequence of epitope (residues) in decreasing likelihood |
|---|---|
| PBP5/1 AAD26697; 679 AA | GTLVYPKLIAD (SEQ ID NO. 41); AYIAGAVILIAA (SEQ ID NO. 42); LKQLGVVPSK (SEQ ID NO. 43); SYQVTRVSDVSQVDLKTALIYSDN (SEQ ID NO. 44); NQAISQSWVQPDYFVPLKII (SEQ ID NO. 45); EKKVLIEHE (SEQ ID NO. 46); GDLLALASSPS (SEQ ID NO. 47); IQEVDGRYYPLGEAAAQLIGYVGDI (SEQ ID NO. 48); GGYFYYQHYQETQAVEA (SEQ ID NO. 49); LQTIVPDLREVVQDV (SEQ ID NO. 50); VEQFVQAL (SEQ ID NO. 51); SELLQYLNQ (SEQ ID NO. 52); HSLSALGIPLAAK (SEQ ID NO. 53); GELLINPIQQAAMYSVF (SEQ ID NO. 54); PNLVFP (SEQ ID NO. 55); AADVKGLQISNLKVD (SEQ ID NO. 56); PNEVLTIN (SEQ ID NO. 57); ITAAIG (SEQ ID NO. 58); SDILLAD (SEQ ID NO. 59); IKAIASSF (SEQ ID NO. 60); YSFSYK (SEQ ID NO. 61); SFLFAF (SEQ ID NO. 62); KVSLTTQ (SEQ ID NO. 63); GELKDLSYKG (SEQ ID NO. 64); PELPAGA (SEQ ID NO. 65); QPFISR (SEQ ID NO. 66); GSTVATT (SEQ ID NO. 67); LDKYQNIY (SEQ ID NO. 68) |
| BML/2 YP_005353284; 360 AA | KVWVIGVD (SEQ ID NO. 69); NFVIIDDVIDGLDNVVSAT (SEQ ID NO. 70); TSTLKAVGTVVEDL (SEQ ID NO. 71); SYLAGVAAAY (SEQ ID NO. 72); EIKVLNQY (SEQ ID NO. 73); TNVVGFIGG (SEQ ID NO. 74); EHTVYGL (SEQ ID NO. 75); SGDVKVPE (SEQ ID NO. 76); GIGYKLKPAIQE (SEQ ID NO. 77); |

TABLE 2-continued

Preferred peptides (epitopes) according to the present invention

| Polypeptide/ SEQ ID No./ Reference Acc No./size of polypeptide | Position/sequence of epitope (residues) in decreasing likelihood |
|---|---|
| | NADIIFHA (SEQ ID NO. 78); KAGVDAG (SEQ ID NO. 79); EDGVGLTEG (SEQ ID NO. 80); KKAVDE (SEQ ID NO. 81) |
| LysM/3 WP_002337891; 197 AA | EHTYVAPVETVEVAPAAPAAATAP (SEQ ID NO. 82); VAEQYVTSR (SEQ ID NO. 83); RIYVGEQLTIP (SEQ ID NO. 84); GRYQLDASYLNGD (SEQ ID NO. 85); LSKISQK (SEQ ID NO. 86) |
| Dala/4 WP_016922432; 435 AA | STVPVVLKSPVKVWVR (SEQ ID NO. 87); SITKIIGLYIVLDQV (SEQ ID NO. 88); AGACFVGT (SEQ ID NO. 89); IITVVLNA (SEQ ID NO. 90); AQDVAIVARHLILDFPEILDVSST (SEQ ID NO. 91); NLSVTPDLSNVPLH (SEQ ID NO. 92); ASMVALAEK (SEQ ID NO. 93); KVNAKAAFAVDAQ (SEQ ID NO. 94); KVSISD (SEQ ID NO. 95); PGFVNYK (SEQ ID NO. 96); VKELFDSAIIQSA (SEQ ID NO. 97); MDYCYD (SEQ ID NO. 98); KANIFVIGWR (SEQ ID NO. 99); QSPVEM (SEQ ID NO. 100); ATIVNAS (SEQ ID NO. 101); ASIPSLKTID (SEQ ID NO. 102); GKILYD (SEQ ID NO. 103); TITLAED (SEQ ID NO. 104) |
| PpiC/5 WP_002291335; 336 AA | YATEYYVVKMV (SEQ ID NO. 105); FEAGLKAHVDI (SEQ ID NO. 106); QSLVQRMIIYKVFNN (SEQ ID NO. 107); ENVLSAF (SEQ ID NO. 108); KSFHPEVEAQIIKLS (SEQ ID NO. 109); TITVSDF (SEQ ID NO. 110); TTKVIGE (SEQ ID NO. 111); DKQVDAE (SEQ ID NO. 112); PAEVKEAAFKL (SEQ ID NO. 113); ESQLEAA (SEQ ID NO. 114); KDQLKDI (SEQ ID NO. 115); SKLAKD (SEQ ID NO. 116); |
| Enol/6 YP_005355275; 432 AA | ANAILGVSIAVARAADYLEVPLYHYLG (SEQ ID NO. 117); GVYVLAD (SEQ ID NO. 118); YTAVVSHR (SEQ ID NO. 119); EVFHALASILKAR (SEQ ID NO. 120); YEELVSKYPIISIE (SEQ ID NO. 121); KAGYVPGKDVVLAMD (SEQ ID NO. 122); ITDVYAREI (SEQ ID NO. 123); LTDVLGDKVQLVGDDLFVTNT (SEQ ID NO. 124); SDIAVATN (SEQ ID NO. 125); EVEVYTE (SEQ ID NO. 126); NSILIKVNQI (SEQ ID NO. 127); AEAIIGYDV (SEQ ID NO. 128); FEVIIEAI (SEQ ID NO. 129); LGEVAEYKGLKSFY (SEQ ID NO. 130); TKVLPT (SEQ ID NO. 131); YNQLLRIE (SEQ ID NO. 132); TKAVDNV (SEQ ID NO. 133); IMPVGAP (SEQ ID NO. 134); YEAVEL (SEQ ID NO. 135) |
| SCP/7 WP_002353118; 685 AA | GGHLVYRLYNK (SEQ ID NO. 136); YNQVHQINLLCNN (SEQ ID NO. 137); QDLLESLGCYGA (SEQ ID NO. 138); KELQVSFSHY (SEQ ID NO. 139); ILGLGHNFVVDSA (SEQ ID NO. 140); GDSVTLTAPSIQGYVLDDR (SEQ ID NO. 141); IYRLFLPGVKSGSHHYTA (SEQ ID NO. 142); TGLYIDDL (SEQ ID NO. 143); VNILKEQIVNVT (SEQ ID NO. 144); NVTVNHV (SEQ ID NO. 145); LEALYTSV (SEQ ID NO. 146); VDNVFISANP (SEQ ID NO. 147); KKPVPTV (SEQ ID NO. 148); LQALYNRV (SEQ ID NO. 149); DHLVKI (SEQ ID NO. 150); NAVLSS (SEQ ID NO. 151); NYFLCRN (SEQ ID NO. 152); NDIVQQAADI (SEQ ID NO. 153); SQAQVN (SEQ ID NO. 154); GQVIATDQAKVTSG (SEQ ID NO. 155); EYTVTIN (SEQ ID NO. 156); NANLLYNNQ (SEQ ID NO. 157); TALSNAKKVLDDS (SEQ ID NO. 158); TFKYKKI (SEQ ID NO. 159); KPKVNKS (SEQ ID NO. 160); DAAFKGLQHK (SEQ ID NO. 161); QNGVAPM (SEQ ID NO. 162); QKQVDS (SEQ ID NO. 163); AKKVLND (SEQ ID NO. 164); RDHHYTA (SEQ ID NO. 165); KAKAFK (SEQ ID NO. 166); DSAYKGL (SEQ ID NO. 167) |
| Adlip/8 | KLKVVVTNSILAD (SEQ ID NO. 10); KIDLHSIVPIGK (SEQ ID NO. 11); TTKVPSLFVESS (SEQ ID NO. 12); GIDVIYLEG (SEQ ID NO. 13); IVTSEGCFKYFSKAYNVPSAYIW (SEQ ID NO. 14); QIKHLVEKL (SEQ ID NO. 15); ADLIFYNGV (SEQ ID NO. 16); IPIYSTI (SEQ ID NO. 17); TKLVKN (SEQ ID NO. 18); YEPLPEDV (SEQ ID NO. 19); GIIYAK (SEQ ID NO. 20); YIEKLDSL (SEQ ID NO. 21) |
| PSB/9 | QSVYPLLKDG (SEQ ID NO. 22); DADVFVYH (SEQ ID NO. 23); IKDQLVKLYPKKAKVFE (SEQ ID NO. 24); HQYTYKYVGYKILN (SEQ ID NO. 25); KSFVTQHAAFGYLALDYGLKQVPIAGL (SEQ ID NO. 26); NVDLMVPAGS (SEQ ID NO. 27); KLEVLNPLESL (SEQ ID NO. 28); GEEVVPEK (SEQ ID NO. 29); LEIVTTFYPMY (SEQ ID NO. 30); FYPASLSKHE (SEQ ID NO. 31); IDFVVNGE (SEQ ID NO. 32); FKYIQFSDHGIAPSKAEHFHIFF (SEQ ID NO. 33); |

TABLE 2-continued

Preferred peptides (epitopes)
according to the present invention

| Polypeptide/<br>SEQ ID No./<br>Reference<br>Acc No./size<br>of<br>polypeptide | Position/sequence of epitope<br>(residues) in decreasing likelihood |
|---|---|
| | LAELKEY (SEQ ID NO. 34);<br>GPNVVEG (SEQ ID NO. 35);<br>HTWVSPK (SEQ ID NO. 36);<br>LDEVFDYK (SEQ ID NO. 37);<br>MILLPG (SEQ ID NO. 38);<br>NYIYFE (SEQ ID NO. 39);<br>YLTKLKRLD (SEQ ID NO. 40) |

Another aspect of the invention thus relates to the polypeptides of the invention or active fragments thereof as described herein, especially for use in medicine, and in particular for use in the prevention and/or treatment of bacterial infection, such as infection by Enterococci.

In a preferred embodiment the polypeptide according to the present invention (according to any of SEQ ID NO: 1 to 9) or the contiguous fragment thereof is used as conjugate, whereby the antigen is covalently bound to an immunocarrier. Such immunocarrier may be a polypeptide or a protein or a carbohydrate-containing molecule (such as for example a capsular polysaccharide or glycoconjugate) which improves the interaction between T- and B-cells for the induction of an immune response against the antigen. This may be preferred for vaccines intended for use in patients with reduced activity of the immune system. Since infections of Enterococci are frequently a problem in hospitals and nursing homes such conjugates are particularly preferred for such patients. Suitable immunocarriers according to the present invention comprise tetanus toxoid, diphtheria toxoid, *Pseudomonas aeruginosa* toxin A or its derivatives thereof. Carbohydrate-containing molecules such as capsular polysaccharides or teichoic acids may also serve as conjugation partner for the above-mentioned polypeptide or fragments thereof. In an especially preferred embodiment such fragments of the immunocarrier are used which stimulate the immune response in the patient to be treated without having, however, the undesired side effect which such proteins may elicit when used in an unmodified form.

The covalent bond between the antigen and the immunocarrier can be provided by a direct chemical bond or by a spacer. Sometimes short molecules having two reactive groups on both ends are reacted with the antigen and the immunocarrier in order to produce a covalently linked molecule.

In an alternative the molecule(s), preferably used as vaccine (antigen and immuno carrier), can be produced recombinantly wherein suitable gene fragments are linked together and inserted into an appropriate vector. The vector is introduced in a suitable host cell and the host cell (e.g. *E. coli*, bacillus, yeast, or insect cells) produces the polypeptide or fragment thereof as defined above together with the immunocarrier as one molecule.

The polypeptides or fragments thereof either alone or coupled to an immunocarrier may be used for the treatment or the prevention of bacterial infections. Another aspect of the present invention thus is a method for the treatment or the prevention of bacterial infections, in particular of Enterococci, more preferably *Enterococcus faecium* based on the medicament as described herein. Said medicament preferably is a vaccine which comprises preferably also a pharmaceutically acceptable adjuvant. The adjuvant promotes the protective IgG subtype antibodies. Typical adjuvants include complete Freund's adjuvant (CFA), incomplete Freund's adjuvant (IFA), alum and other adjuvants suitable for human use (e.g. virus-like particles). Polymers like dextran sulfate have been shown to be also a potent stimulator of IgG antibodies against bacterial cell surface antigen. Other adjuvants include incomplete adjuvants; salt i.e. $AlK(SO_4)_2$, $AlNa(SO_4)_2$, $AlNH_4(SO_4)_2$, solica, kaolin, carbon polynucleotide, i.e. poly IC and poly AU. Preferred adjuvants include QuilA and Alhydrogel.

An active vaccine is administered to the patient preferably before an infection occurs. Such vaccination can therefore be applied regularly to patients at risk (e.g. elderly people, patients before solid organ or bone-marrow transplants) in order to stimulate their immune response and to avoid an infection in a hospital or a nursing home.

Medicaments and/or vaccines according to the present invention contain at least one polypeptide or active fragment thereof, but can contain 2 to up to 9 full length polypeptides according to the present invention. Preferred is a vaccine comprising at least one "set" of active fragments of at least one antigen according to the present invention, wherein said set is composed of 1, 2, 3 and up to 10 active fragments of said at least one antigen according to the present invention. The vaccine may also contain a mix of active fragments derived from antigens according to the present invention, i.e. SEQ ID Nos. 1 to 9. Preferred is a composition comprising at least one of the antigens (epitopes) as listed in table 2, above.

Under specific circumstances it may, however, also be possible to apply the vaccine at early stages of the infection in order to elicit protective antibodies which inactivate the bacteria belonging to the genus *Enterococcus*. In a preferred embodiment the vaccine of the present invention provides protection against different *Enterococcus faecium* and possibly also against *Enterococcus faecalis* strains since there is extensive sequence homology between these species.

Antibodies induced by the protein of SEQ ID NO: 1 to 9 or suitable fragments thereof are protective and facilitate phagocytosis. Since such protective, and in particular opsonic antibodies, are preferred, it is desired to use those parts of the polypeptide of SEQ ID NO:1 to 9 which elicit antibodies having opsonic properties.

As mentioned above, still another subject of the invention is a pharmaceutical composition, especially a vaccine, comprising the protective peptide or active fragments thereof or the antibody or functional fragments thereof as defined by the invention, useful for the immunization of a subject against an infection or the treatment of a subject having an infection, wherein the infection is preferably caused by *E. faecium* and/or *E. faecalis*. This pharmaceutical formulation of a medicament to be used as a vaccine is known to the person skilled in the art, and described in the respective literature. Usually, a solution of the antigen possibly coupled to an immunocarrier is dissolved in a physiologically acceptable solution like a buffer. The solution must be stabilized in order to avoid an undesired precipitation of the immunologically active compounds. The vaccine is preferably produced in the form of a solution adapted to injection, preferably intramuscular injection. Other forms of pharmaceutical formulations like plasters or sprays are also acceptable provided the antigen comes in sufficient contact with the immune system and the formation of specific antibodies is elicited.

Alternatively, the peptide or active fragments thereof of the invention are used in a method of immunizing or treating a subject in need thereof, wherein an effective amount of the peptide or the nucleic acid of the invention is administered to the subject. The subject may be immunized in order to prevent an infection, particularly an *E. faecium* and/or *E. faecalis* infection, or may be treated to ameliorate or cure an infection, particularly an *E. faecium* and/or *E. faecalis* infection. The determination of the effective amount to be administered is within the knowledge of the skilled practitioner.

The polypeptides or fragment thereof either alone or coupled to an immunocarrier may be used for the treatment or the prevention of bacterial infections. The prevention of bacterial infection achieved by regularly application of the vaccine to patients of risk such as elderly people, infants and patients before organ or bone-marrow transplantation so antibodies had been generated though the stimulation of the immune response.

The vaccine is preferably produced in the form of a solution adapted to injection, preferably intramuscular injection. Other forms of pharmaceutical formulations like plasters or sprays are also acceptable provided the antigen comes in sufficient contact with the immune system and the formation of specific antibodies are elicited.

On the other hand, it is sometimes not possible to treat patients with an active vaccine since the immune system is severely impaired. In those circumstances the polypeptide of SEQ ID NO: 1 to 9 or fragments thereof (epitopes) as defined above can be used to produce either polyclonal antibodies or monoclonal antibodies that bind to or opsonize *Enterococcus*. The person skilled in the art is well aware how such antibodies can be prepared.

The inoculum for polyclonal antibody production is typically prepared by dispersing the antigen or the antigen-immunocarrier conjugate in a physiologically tolerable diluent such as saline, to form an aqueous composition. An immunostimulatory amount of the inoculum preferably with adjuvant is administered to a mammal and the inoculated mammal is then maintained for a time period sufficient for the antigen to induce protective anti-*Enterococcus* antibodies. After suitable periods of time, two weeks until four months, boosting doses of the antigen-immunocarrier may be applied and the antigen titer is monitored. At a suitable point, when the titer of the neutralizing or opsonic antibodies is at its peak, the antibodies are collected. Such antibodies can include antibody preparations from a variety of commonly used animals (such as mice, goats, primates, donkeys, rabbits or horses) and humans, whereby the antibodies are isolated from blood donations.

The antibodies induced in the mammal are harvested, isolated and purified to the extent desired by well-known techniques such as by alcohol fractionation and column chromatography or preferably by immuno affinity chromatography whereby the antigen is bound to a chromatographic column. The antiserum passes the column whereby specific antibodies are retained and all other components of the serum are washed out. Then the purified antibodies are eluted with suitable gradients. A further purification may be required.

Alternatively, monoclonal antibodies can be prepared according to techniques well-known to the person skilled in the art. When a suitable monoclonal antibody is obtained, the binding regions can be identified and the whole antibody molecule as well as derivatives of the antibody like antibody fragments or subfragments can be provided. The general technique to produce monoclonal antibodies is amply described in textbooks. After having made the hybridomas or having selected the monoclonal antibody from libraries or genetically engineered animals it has to be determined to which part of the polypeptide of SEQ ID NO: 1 to 9 the mAb binds. Then, it has to be checked whether the antibody is opsonic and/or protective, preferably in vivo.

According to another preferred aspect of the present invention, it would be very beneficial to provide monoclonal or polyclonal antibody therapies which target antigenic polypeptides of *E. faecium* and/or *E. faecalis* as described herein and have the potential to support a therapy of an infection or eliminate the pathogen and the disease altogether. Therefore, another subject of the invention relates to an antibody or functional active fragment thereof which binds specifically to the antigens of the invention. In a preferred embodiment the antibody is a monoclonal, polyclonal, chimeric or humanized antibody or functional active variant thereof. In another preferred embodiment the functional active fragment comprises a Fab fragment. Antibodies generated against the antigens (polypeptides), fragments or variants thereof of the present invention can be obtained by direct injection of the antigens, fragments or variants thereof into an animal or by administering the antigens, fragments or variants thereof to an animal, preferably a non-human. The antibody so obtained will then bind the antigens, fragments or variants. Such antibodies can then be used to isolate reactive antigens, fragments or variants thereof from tissue expressing those.

For the preparation of monoclonal antibodies, any technique known in the art, which provides antibodies produced by continuous cell line cultures, e.g. a hybridoma cell line, can be used. Techniques described for the production of single chain antibodies (U.S. Pat. No. 4,946,778) can be adapted to produce single chain antibodies to the antigens, fragments or variants thereof according to this invention. Also, transgenic mice or other organisms such as other mammals may be used to express humanized antibodies to antigens, fragments or variants thereof according to this invention. Still another subject of the invention relates to a hybridoma cell line which produces the antibody of the invention. Hybridoma cell lines expressing desirable monoclonal antibodies are generated by well-known conventional techniques. Similarly, desirable high titer antibodies are generated by applying known recombinant techniques to the monoclonal or polyclonal antibodies developed to these antigens (see, e.g., PCT Patent Application No. PCT/GB85/00392; British Patent Application Publication No. GB2188638A; Amit et al., Science, 233:747-753 (1986); Queen et al., Proc. Natl. Acad. Sci. USA, 86: 10029-10033 (1989); WO 90/07861; Riechmann et al., Nature, 332:323-327 (1988); Huse et al., Science, 246:1275-1281 (1988)).

The present invention also provides a method for producing an antibody according to the invention, characterized by the following steps:
(a) administering an effective amount of the peptide according to the invention to an animal; and
(b) isolating the antibody produced by the animal in response to the administration of step (a) from the animal.

Another subject of the invention relates to a method for producing an antibody according to the invention, characterized by the following steps:
(a) contacting a B cell with an effective amount of the peptide according to the invention;
(b) fusing the B cell of step (a) with a myeloma cell to obtain a hybridoma cell; and
(c) isolating the antibody produced by the cultivated hybridoma cell. More particularly, the antibody may be produced by initiating an immune response in a non-human animal by administrating a peptide of the invention to an animal, removing an antibody containing body fluid from said animal, and producing the antibody by subjecting said antibody containing body fluid to further purification steps. Alternatively, the antibody may be produced by initiating an immune response in a non-human animal by administrating an antigen, fragment or variant thereof, as defined in the present invention, to said animal, removing the spleen or spleen cells from said animal and/or producing hybridoma cells of said spleen or spleen cells, selecting and cloning hybridoma cells specific for said antigen, fragment or variant thereof and producing the antibody by cultivation of said cloned hybridoma cells.

The antibody may be used in methods for treating an infection. Accordingly, still another subject of the invention relates to a pharmaceutical composition comprising the antibody of the invention. The pharmaceutical composition may encompass further components as detailed above for the vaccine. The composition may further encompass substances increasing their capacity to stimulate T cells. These include T helper cell epitopes, lipids or liposomes or preferred modifications as described in WO 01/78767. Another way to increase the T cell stimulating capacity of epitopes is their formulation with immune stimulating substances for instance cytokines or chemokines like interleukin-2, -7, -12, -18, class I and II interferons (IFN), especially IFN-gamma, GM-CSF, TNF-alpha, flt3-ligand and others.

Medicaments according to the present invention contain at least one antibody or active fragment thereof, but can contain 2 to up to 9 antibodies according to the present invention. Preferred is a medicament comprising at least one "set" of antibodies or active fragments thereof specifically directed against at least one antigen according to the present invention, wherein said set is composed of 1, 2, 3 and up to 10 antibodies or active fragments thereof specifically directed against said at least one antigen according to the present invention. Of course, also mixtures of antibodies or active fragments thereof specifically directed against 2, 3, and up to 9 of the antigens according to the present invention can be formulated into a medicament according to the present invention.

The polypeptides according to the present invention do not show significant differences in the percentage of killing, but preferred are the polypeptides according to the present invention showing a higher or equal activity at a higher dilution, namely Adlip (SEQ ID No. 8), PBP5 (SEQ ID No. 1), and PpiC (SEQ ID No. 5) (which are thus preferred). It is expected that a lower concentration of the antigen decreases and/or reduces the risk of prospective side effects.

The present invention will now be described further in the following examples with reference to the accompanying Figures and the Sequence Listing, nevertheless, without being limited thereto. For the purposes of the present invention, all references as cited herein are incorporated by reference in their entireties.

Figure 1:
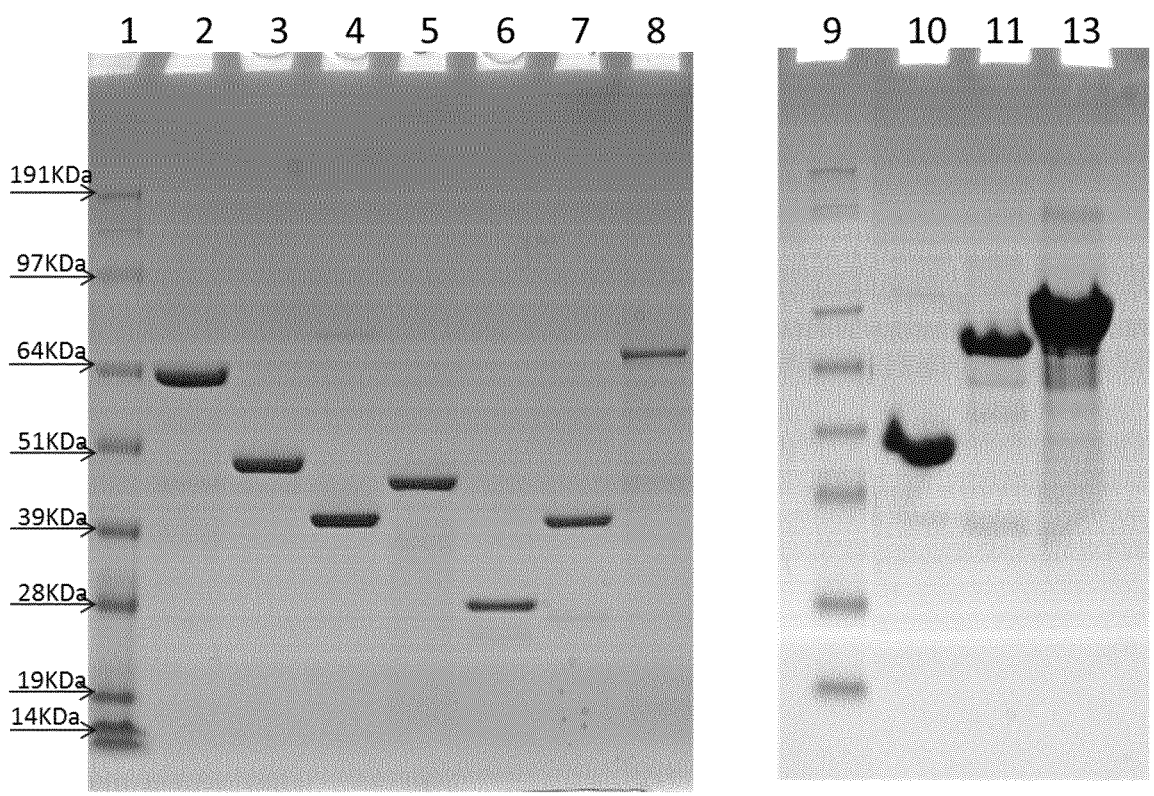
FIG. 1 shows an SDS-PAGE gel stained with Coomassie Brilliant Blue of proteins purified by Protino® Ni-NTA Agarose. Lanes: 1 and 9: MW Standard; 2: Sag A; 3: Enol; 4: PpiC; 5: Dala; 6: LysM; 7: BML; 8: PBP5; 10: Adlip; 11: PSB and 12: SCP.

SEQ ID NOs: 1 to 9 show the amino acid sequence of the polypeptides according to the invention derived from strain *Enterococcus faecium* E155, and *Enterococcus faecalis*. SEQ ID NOs: 10 to 167 show the amino acid sequence of preferred peptide fragments (epitopes) as active fragments derived from the polypeptides according to the invention.

EXAMPLES

The bacterial strain used for all experiments was the Vancomycin-resistant *E. faecium* E155 strain, a clinical isolate that belongs to a genetic subpopulation of hospital-associated *E. faecium* responsible for worldwide emergence due to its multidrug-resistance and especially high level resistance to quinolone and ampicillin.

Example 1

Identification and Extraction of the Polypeptides According to the Present Invention 1. Surface Protein Extraction Using Trypsin Shaving Method Extractions were performed as described by Tjalsma et al. (2008). Briefly, two aliquots of 50 ml of bacterial cultures of the E155 strain were harvested at $OD_{600}=0.4$ by centrifugation (10,000 rpm., 2 min) and washed twice with 4 ml Bicam (triethylammonium bicarbonate buffer 100 mM pH 8). The first aliquot was then mixed with a solution of trypsin in Bicam at final concentration of 10 µg/mL. The other aliquot was resuspended in Bicam without any trypsin. All the samples were incubated for 1 h at 37° C. under gentle shaking. After centrifugation (7,500 rpm., 5 min), the cell pellets were removed, and the supernatants were treated with 1 mM DTT for 30 min, followed by 1 mM iodoacetamide (IAA), also for 30 min at room temperature. Finally, fresh trypsin (0.5 mg) was added to all samples and tryptic cleavage was continued for 18 h at 37° C. In this way two samples were obtained for each experiment. These "shaved" proteins were identified by LC-MS/MS. For this protocol, the inventors analyzed 25 different conditions using different amounts of trypsin, different times of incubation with the enzyme and additional combined treatments with lysozyme and/or mutanolysin.

After analysis of the 25 samples as obtained using the different conditions by nanoLC-MS/MS, a total of 401 proteins was identified using the Mascot software databases. Overall, 34 proteins were identified as surface proteins, 29 as present in both intra- and extracellular location, 315 as cytoplasmic proteins and 23 of unknown location. The results of this method demonstrate that this procedure is not an appropriate strategy to obtain mostly surface proteins, since only around 16% of the identified proteins belong to this category. Furthermore, this procedure is not an appropriate strategy as the sole strategy to obtain target polypeptides.

2. Extraction of Surface Proteins Under Strong Alkaline Conditions

Surface-exposed proteins were extracted by exposure of cells to high pH using a protocol described by Hempel et al. (2011). Briefly, a cell pellet from a 50 ml culture ($OD_{600}$=0.5) was washed with a PBS sucrose solution [NaCl 100 mM, sucrose 60 mM, sodium phosphate 55 mM (pH 7.2)] and then shaken gently for 1 h at room temperature in 2 ml NaOH glycine sucrose [glycine 50 mM, sucrose 60 mM (pH 12.4)]. After centrifugation (30 min, 10,000 g), 108 ml 1 M HCl and 100 ml 1 M Tris/HCl (pH 7.0) were added to 1 ml supernatant. Proteins were precipitated at 4° C. by addition of 8 ml cold acetone. The protein pellet obtained after centrifugation (10 min, 10,000 g) was resuspended in 20 ml Tris/HCl (pH 7.5).

This protocol was used to extract peripheral proteins that are loosely attached to the membrane or cell wall. These proteins can be detached using treatment with a polar reagent like an alkaline pH solution since they are non-covalently attached to either the lipid layer or to integral membrane proteins by hydrophobic, electrostatic, or other interactions. Two different media where tested for this procedure, TSB and GM17, which are both rich laboratory mediums. The samples obtained under the different conditions were analyzed by nanoLC-MS/MS. A total of 329 proteins were identified using the mascot software databases. Overall, 47 proteins were identified as surface proteins, 16 as present in both intra- and extracellular location, 246 as cytoplasmic proteins and 20 of unknown location. As this method let to the isolation of intact proteins, the inventors were able to test their immunogenicity by immunodotblot and western blot. However, the results demonstrate that this method is also not the best strategy to obtain samples enriched in surface proteins because just around 19% of the predicted proteins belong to this category. Thus, this procedure is also not an appropriate strategy as the sole strategy to obtain target polypeptides.

3. Surface Proteins Extraction Using Biotinylation

Surface-exposed proteins were labeled and extracted by exposure of cells to Sulfo-NHS-SS-Biotin using a protocol described by Hempel et al. (2011). Briefly, 100 mL of bacterial cultures at $OD_{600}$=0.5 were harvested at 8,000×g for 5 min at 4° C. 0.2 g of cells (wet cell weight) were resuspended in 5 mL ice-cold PBS (pH 8.0) with 1 mM PMSF on ice. The biotinylation reaction was performed by adding 100 µL fresh Sulfo-NHS-SS-Biotin solution to 1 mL of intact cells, to give a final concentration of 1.5 mM Sulfo-NHS-SS-Biotin. A 1% (w/v) solution of Sulfo-NHS-SS-Biotin was prepared by adding 5 mg to 500 µL PBS (pH 8.0) immediately before use. Cells were incubated by gentle shaking for 1 h on ice. To stop the reaction and to remove nonreacted biotinylation reagent, cells were centrifuged at 8500×g for 1 min at 4° C. and washed three times with ice-cold PBS (pH 8.0)/500 mM glycine. A pellet of 1 mL reaction volume was resuspended in 500 µL PBS (pH 8.0) with 1 mM PMSF on ice and transferred to a 1.5 mL tube containing glass beads. The disruption of cells was performed mechanically in a FastPrep cell disrupter at 6 m/s$^2$ twice for 30 s. The cell debris was recovered from the glass beads with a total of 3 mL of PBS (pH 8.0). The lysate was centrifuged (100,000×g for 1 h at 4° C.). The supernatant was then discarded. The cell debris were resuspended in a total of 400 µL of [PBS (pH 8.0), IAA (5%)] and homogenized in a FastPrep cell disrupter at 6 m/s$^2$ twice for 30 s with 0.25 ml of glass beads. The proteins were then solubilized by addition of 100 µL of PBS (pH 8.0) with 1 mM PMSF, 4% CHAPS and 2% ASB-14. A second homogenization step was performed after detergent addition under the same conditions as mention above. Cell debris was removed by centrifugation (14,000 rpm, 15 min) after 1 h of incubation with the detergent.

The biotinylated proteins were isolated and purified by NeutrAvidin agarose affinity-purification. For a reaction volume of 500 µL protein mixture 150 µL of NeutrAvidin agarose resin were washed twice with PBS (pH 8.0)/1% NP-40 and centrifuged at 1,000 rpm for 1 min at 4° C. The resin was mixed with the cell lysate for 1 h by gently shaking on ice. The supernatant was removed and the resin-bound complex washed 6 times with PBS (pH 8.0)/1% NP-40. Biotinylated proteins were eluted twice by incubation with 1 mL of elution buffer (5% mercaptoethanol in $H_2O$) for 1 h with gentle shaking; supernatant was recovered after centrifugation at 1,000 rpm for 1 min and poured to 8 mL of cold acetone (−20° C., overnight). The precipitated proteins were harvested by centrifugation (8,500 rpm, 30 min, 4° C.) and washed twice with 1 mL of cold 98% ethanol (4° C.). The pellets were dried in a SpeedVac for 2 min and dissolved in 15 µl 6M urea/2M thiourea for 2 min at 80° C. The samples were loaded on a SDS-PAGE gel and the corresponding bands were excised from the gel and dehydrated with acetonitrile. Afterwards, samples were reduced and alkylated in two successive steps of 20 min with 0.5% Dithiothreitol and 5% Iodoacetamide. Samples were washed twice with 30% acetonitrile, 200 mM ammonium bicarbonate and subsequently digested overnight with 0.2 µg of trypsin (Promega). Peptides were obtained by covering the gel bands with water and incubating them in an ultrasonic bath for 15 min. Finally peptides samples were analyzed by nanoLC-MS/MS, sequence data were compared to the NCBI and MASCOT databases.

Three different media where tested for this approach, the rich laboratory medium TSB, ccM17 MOPS, a carbon depleted laboratory medium and BHI (brain hearth infusion) medium supplemented with 30% of horse serum to mimic in vivo conditions. The samples obtained under the different conditions were analyzed by nanoLC-MS/MS. A total of 45 proteins were identified using the Mascot software databases. Overall, 27 proteins were identified as surface proteins, 6 as present in both intra and extra cellular location, and 12 as cytoplasmic proteins. The combined results demonstrated that this procedure is the best strategy to target preferentially surface proteins since 73% of the predicted proteins belonged to this category. Nevertheless, for the purposes of the present invention, all three approaches were combined.

4. Additional Surface Protein Identification from Transcriptional Analysis

Real-time PCR experiments performed with cDNA synthesized from RNA extracted from an in vivo endocarditis model in E. faecalis closely related species revealed that over 300 genes were up-regulated under these conditions. Among these, 19 genes were identified to encode surface related proteins. These proteins were analyzed by online BLAST in the J. Craig Venter Institute database comparing the sequences in E. faecium completely sequenced strains.

The adhesion lipoprotein (Adlip) and a protein showing homology to a periplasmic solute binding protein (PSB) were identified as the closest surface proteins related between the two strains and selected as targets for the overexpression experiments (see below).

6. MS Analyses

MS analyses were performed after the overnight tryptic cleavage of protein samples obtained by shaving extraction. Trypsin-cleaved samples were desalted and concentrated on a tipmicroC18 Omix (Varian) before nano-liquid chromatography (LC)-MS-MS analysis. The chromatography step was performed using a Prominence nano-LC system (Shimadzu).

7. Summary of all the Extraction Methods

A comparison between the proteins identified with the three methods allowed the inventors to establish that 22 extracellular proteins were detected by two of the three methods as used, and seven by all of them. Sag A was used as a control. Finally, nine proteins were selected for overexpression (see table 2). Seven of them were identified by the three extraction methods and the remaining two identified to be induced in vivo in the closely related species *E. faecalis*.

Overexpression and purification of the H6-proteins. A QIAexpress system was used for the expression of a six-His-tagged recombinant proteins as follows. First, the genes were amplified by PCR using primers designed at the beginning of each gene (excluding the signal peptide base pairs) and one at the end of it. The PCR product was digested using the endonucleases BamHI and PstI for the genes encoding SagA, LysM, Dala, PpiC, Enol, Adlip and PSB; and BamHI and SacI for SCP, PBP5, BML and PpiC; and cloned into the corresponding restriction sites of the respective plasmid: pQE30 or pET28a+. The resulting plasmid, were then introduced in *E. coli* M15(pREP4) cells for the pQE30 and in *E. coli* BL21 for the pET28a+. Colonies were screened by PCR and the integrity of the constructions was controlled by sequencing.

2. Overexpression and Purification of the Protein

The overexpression of all the proteins was carried out by inoculating an overnight culture in fresh LB media supplemented with the corresponding antibiotic. Bacteria were grown during 2 hours at 37° C. and shaking at 160 rpm before induction of protein expression by 0.5 mM IPTG, then, the culture was incubated for two additional hours under the same conditions. Cells were harvested by centrifugation and later disrupted using lysozyme and the

TABLE 2

Comparison of the proteins identified by the different extraction methods

| Protein | Abbreviation | Locus Tag | Method |
|---|---|---|---|
| low affinity penicillin-binding protein 5 (PBP5) | PBP5 | EFAU004_00870 | Biotin, High pH, Trypsin |
| Basic membrane lipoprotein | BML | EFAU004_00080 | Biotin, High pH, Trypsin |
| peptidoglycan-binding protein LysM | LysM | EFAU004_01059 | Biotin, High pH, Trypsin |
| D-alanyl-D-alanine carboxypeptidase | Dala | EFAU004_01127 | Biotin, High pH, Trypsin |
| PpiC-type peptidyl-prolyl cis-trans isomerase | PpiC | EFAU004_02526 | Biotin, High pH, Trypsin |
| Enolase | Enol | EFAU004_02073 | Biotin, High pH, Trypsin |
| SCP-like extracellular protein (serine protease) | SCP | WP_002353118.1 | Biotin, High pH, Trypsin |
| Adhesion lipoprotein | Adlip | EFUG_02345 | Biotin, High pH, Transcriptomic data |
| Periplasmic solute binding family | PSB | EFAU004_00598 | Biotin, High pH, Transcriptomic data |

Example 2

Overexpression of the Polypeptides and Production of Polyclonal Antibodies

1. Cloning of the Genes Encoding the Protein Candidates

The genes encoding the selected proteins were identified by in silico analysis using the *E. faecium* E155 genome sequence. Overexpression of the proteins was performed by cloning the corresponding genes into the expression vectors pQE30 or pET28a+. For the PBP5, BML, LysM, Dala, PpiC, Enol, PSB and Adlip the vector pQE30 was used, and the pET28a+ for the SCP. In addition, one more protein was overexpressed and purified, the Sag A protein supposed to be a promising vaccine target in *E. faecium* (Kropec et. al, 2011) was included as a positive control.

FastPrep cell disrupter. Proteins were purified under denaturing conditions using Protino® Ni-NTA Agarose following the instructions of the manufacturer (Macherey-Nagel).

Purified proteins were subject of SDS-PAGE with 10% acrylamide/bisacrylamide resolving gels (NuPAGE, Invitrogen) and stained with Coomassie brilliant blue (SimplyBlue SafeStain, Invitrogen) for protein detection and molecular size confirmation (see FIG. 1). Coomassie blue-stained bands were excised from the gel and treated in the same way as described before for nano LC-MS/MS analysis (see biotinylation procedure).

Example 3

1. Production of Polyclonal Antibodies

In order to produce anti-protein hyperimmune serum, eight New Zealand White rabbits (2.5 to 3.5 kg; Charles River Laboratories) were vaccinated with each protein (Enol, PpiC, Dala, LysM, BML, PBP5, Adlip and PSB) according to the immunization schedule (see Table 3). Preimmune serum was collected from the rabbits on days 0 and 7 prior to the first vaccination to be used as a negative control.

TABLE 3

Immunization schedule for purified polypeptides
Schedule for the immunization with the polypeptide

| Day No. | Procedure |
|---|---|
| 0 | Pre Bleed 10-15 mL |
| 7 | Pre Bleed 10-15 mL |
| 14 | Immunization 1 s.c. (1FIA) 10 ug |
| 28 | Immunization 2 s.c. (1FIA) 10 ug |
| 35 | Boost 1 i.v. 5 ug (without FIA) |
| 37 | Boost 2 i.v. 5 ug (without FIA) |
| 39 | Boost 3 i.v. 5 ug (without FIA) |
| 53 | Test Bleed 2-10 mL |
| 60 | Boost 4 i.v. 5 ug (without FIA) |
| 67 | Boost 5 i.v. 5 ug (without FIA) |
| 74 | Terminal Bleed |

The sera were heat inactivated at 56° C. for 30 min and were then absorbed 1 h with heat killed cells of *E. faecium* E1162 treated with proteinase K.

2. Opsonophagocytic Assays

An in vitro opsonophagocytic assay (OPA) was performed as described elsewhere (Huebner J, 1999) using baby rabbit serum as complement source and rabbit serum raised against purified proteins. Polymorphonuclear neutrophils (PMN's) were freshly prepared from human blood collected from healthy adult volunteers. Bacterial strains were grown to mid-log phase in TSB. For the assay, the following components were mixed: 100 µl of PMNs; 100 µl of 1:10 and 1:50 serum dilution, 100 µl of absorbed baby rabbit complement 1:30 dilution, and 100 µl of 1:150 dilution of bacteria *E. faecium* E155. The mixture was incubated on a rotor rack at 37° C. for 90 min, and samples were plated in duplicate at time 0 and after 90 min. Percent killing was calculated by comparing the colony counts of a control without PMN's to the colony counts after a 90-minute incubation at 37° C. (T90). For inhibition studies, rabbit serum was diluted 1:50 or 1:100 and incubated for 60 min at 4° C. with an equal volume of a solution containing 100 µg of the corresponding protein. Subsequently, the antiserum was used in the OPA as described above. Inhibition assays were performed at serum dilutions yielding 50-60% killing of the inoculum without the addition of the inhibitor. The percentage of inhibition of opsonophagocytic killing was compared to controls without inhibitor.

Figure 2:
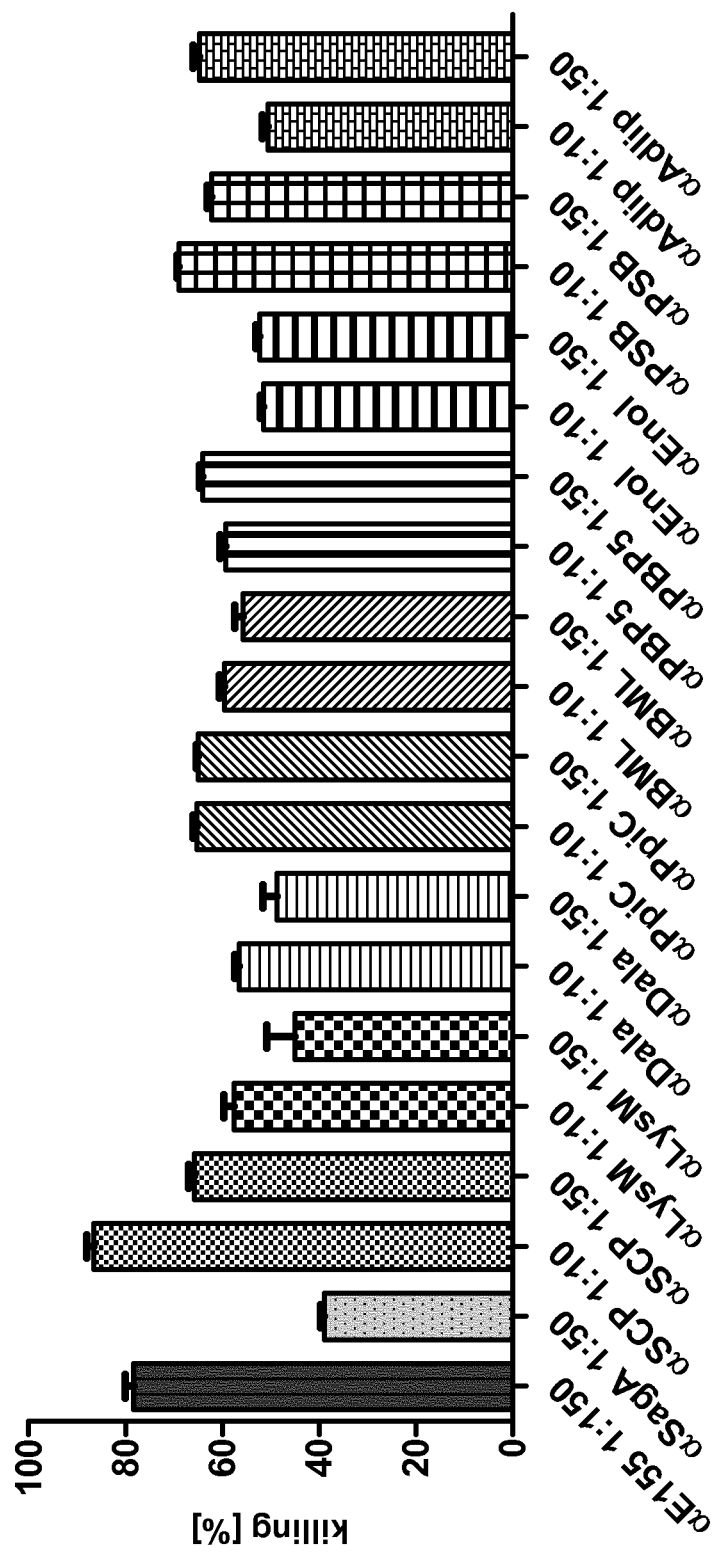
FIG. 2 shows opsonic killing of a polyclonal rabbit antisera produced in rabbits against the whole bacterial cell of *Enterococcus faecium* E155. Different dilutions (1:50 and 1:100) of the sera were tested. The substantial opsonic activity of the antibodies as raised is represented by the bars. Bars represent data means for the observations, and the error bars indicates the SEM for each protein. SagA was used as positive control known as promising vaccine target in *E. faecium*.
Figure 3:
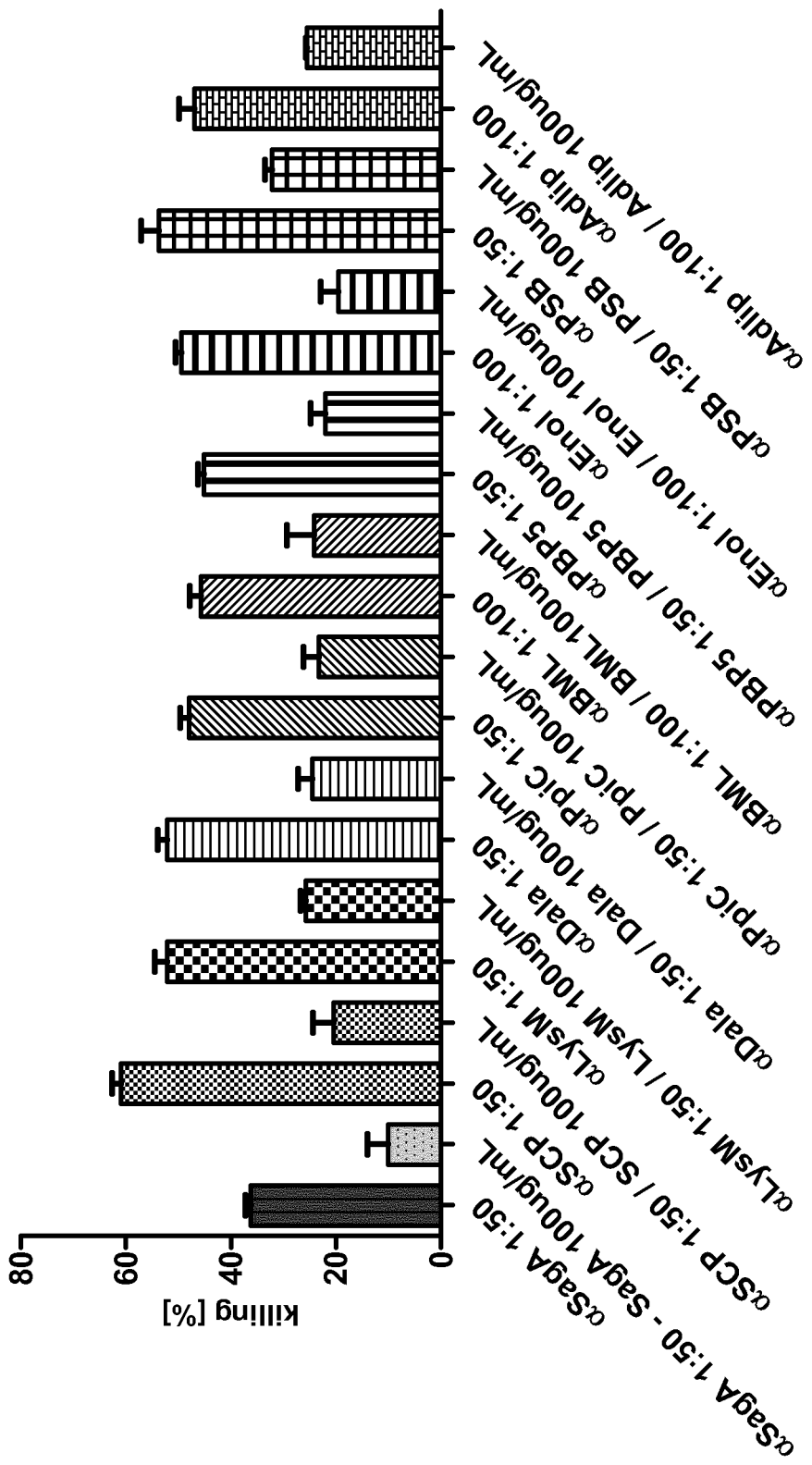
FIG. 3 shows an opsonophagocytic inhibition assay with serum raised against recombinant proteins using 100 µg of purified protein for absorptions. Bars represent data means for the observations, and the error bars indicates the SEM for each protein. SagA was used as a positive control. However, the opsonic killing activity of the polypeptides of the present invention is notably stronger.

The results are shown in FIGS. 2 and 3.

REFERENCES AS CITED

Leclercq R., Derlot E., Duval J., Courvalin P. (1988). Plasmid-mediated resistance to vancomycin and teicoplanin in *Enterococcus faecium*. N Engl J Med 319, 157-61.

Murray B E. (2000). Vancomycin-resistant enterococcal infections. N Engl J Med. 342, 710-21.

Chatterjee I., Iredell J R., Woods M., Lipman J. (2007). The implications of enterococci for the intensive care unit. Crit Care Resusc. 9, 69-75.

Hidron A I., Edwards J R., Patel J., Horan T C., Sievert D M., Pollock D A., Fridkin S K.; National Healthcare Safety Network Team; Participating National Healthcare Safety Network Facilities. (2008). NHSN annual update: antimicrobial-resistant pathogens associated with health-care-associated infections: annual summary of data reported to the National Healthcare Safety Network at the Centers for Disease Control and Prevention, 2006-2007. Infect Control Hosp Epidemiol. 11, 996-1011.

Malani P N., Dyke D B., Pagani F D., Chenoweth C E. (2002). Nosocomial infections in left ventricular assist device recipients. Clin Infect Dis. 34, 1295-1300.

Sette A., Rappuoli R. (2010). Reverse vaccinology: developing vaccines in the era of genomics. 3, 530-541.

Tjalsma, H., Lambooy, L., Hermans, P. W. & Swinkels, D. W. (2008). hedding & shaving: disclosure of proteomic expressions on a bacterial face. Proteomics 8, 1415-1428.

Hempel, K., Herbst, F.-A., Moche, M., Hecker, M. & Becher, D. (2011). Quantitative proteomic view on secreted, cell surface associated, and cytoplasmic proteins of the methicillin-resistant human pathogen *Staphylococcus aureus* under iron-limited conditions. J Proteome Res 10, 1657-1666.

Kropec A, Sava I G, Vonend C, Sakinc T, Grohmann E, Huebner J. (2011). Identification of SagA as a novel vaccine target for the prevention of *Enterococcus faecium* infections. Microbiology. 157, 3429-3434.

Huebner J, Wang Y, Krueger W A, Madoff L C, Martirosian G, Boisot S, Goldmann D A, Kasper D L, Tzianabos A O, Pier G B. (1999). Isolation and chemical characterization of a capsular polysaccharide antigen shared by clinical isolates of *Enterococcus faecalis* and vancomycin-resistant *Enterococcus faecium*. Infect Immun 67, 1213-1219.

The invention claimed is:

1. A method for inducing in a subject opsonic antibodies against at least one polypeptide selected from the group consisting of SEQ ID NOs: 1 and 3-9, for treatment of an *Enterococcus* infection that can be treated by such opsonic antibodies, wherein the method comprises administering to the subject in need of such treatment, a composition comprising an effective amount of at least one polypeptide selected from the group consisting of SEQ ID NOs: 1 and 3-9 to induce opsonic antibodies in the subject; and confirming opsonic antibodies against at least one polypeptide selected from the group consisting of SEQ ID NOs: 1 and 3-9 in the subject through testing a serum sample for opsonic killing activity.

2. The method according to claim 1 wherein said polypeptide is covalently bound to a protein, a carbohydrate, and/or a glycoconjugate.

3. The method according to claim 1, wherein the composition comprises at least one pharmaceutically acceptable adjuvant.

4. The method according to claim 1, wherein the composition is a vaccine.

5. A polypeptide selected from the group consisting of SEQ ID NOs: 1 and 3-9, wherein said polypeptide is covalently bound to an immunocarrier.

6. The method, according to claim 1, wherein the infection is caused by *E. faecium* or *E. faecalis*.

7. The method, according to claim 4, wherein said vaccine is against an infection caused by *Enterococcus faecium* or *E. faecalis*.

8. The polypeptide, according to claim 5, wherein said immunocarrier is a protein, a carbohydrate, and/or a glycoconjugate.

9. The method according to claim 1, wherein the *Enterococcus* infection is caused by an *Enterococcus* bacterium expressing a polypeptide comprising any one of SEQ ID NOs: 1 and 3-9.

10. The method according to claim 1, wherein the subject is a human.

11. The method according to claim 1, wherein the composition comprises an effective amount of at least one polypeptide selected from the group consisting of SEQ ID NO: 7 and SEQ ID NO: 9.

12. The polypeptide according to claim 5, which has an amino acid sequence selected from the group consisting of SEQ ID NOs: 7 and 9.

* * * * *

SEQUENCE LISTING

<160> NUMBER OF SEQ ID NOS: 167

<210> SEQ ID NO 1
<211> LENGTH: 678
<212> TYPE: PRT
<213> ORGANISM: Enterococcus faecium

<400> SEQUENCE: 1

```
Met Lys Arg Ser Asp Lys His Gly Lys Asn Arg Thr Gly Ala Tyr Ile
1               5                   10                  15

Ala Gly Ala Val Ile Leu Ile Ala Ala Ala Gly Gly Gly Tyr Phe Tyr
            20                  25                  30

Tyr Gln His Tyr Gln Glu Thr Gln Ala Val Glu Ala Gly Glu Lys Thr
```

```
            35                  40                  45
Val Glu Gln Phe Val Gln Ala Leu Asn Lys Gly Asp Tyr Asn Lys Ala
 50                  55                  60

Ala Glu Met Thr Ser Lys Lys Ala Ala Asn Lys Ser Ala Leu Ser Glu
 65                  70                  75                  80

Lys Glu Ile Leu Asp Lys Tyr Gln Asn Ile Tyr Gly Ala Ala Asp Val
                     85                  90                  95

Lys Gly Leu Gln Ile Ser Asn Leu Lys Val Asp Lys Lys Asp Asp Ser
                    100                 105                 110

Thr Tyr Ser Phe Ser Tyr Lys Ala Lys Met Asn Thr Ser Leu Gly Glu
                    115                 120                 125

Leu Lys Asp Leu Ser Tyr Lys Gly Thr Leu Asp Arg Asn Asp Gly Gln
            130                 135                 140

Thr Thr Ile Asn Trp Gln Pro Asn Leu Val Phe Pro Glu Met Glu Gly
145                 150                 155                 160

Asn Asp Lys Val Ser Leu Thr Thr Gln Glu Ala Ala Arg Gly Asn Ile
                    165                 170                 175

Ile Asp Arg Asn Gly Glu Pro Leu Ala Thr Thr Gly Lys Leu Lys Gln
                180                 185                 190

Leu Gly Val Val Pro Ser Lys Leu Gly Asp Gly Gly Glu Lys Thr Ala
            195                 200                 205

Asn Ile Lys Ala Ile Ala Ser Ser Phe Asp Leu Thr Glu Asp Ala Ile
210                 215                 220

Asn Gln Ala Ile Ser Gln Ser Trp Val Gln Pro Asp Tyr Phe Val Pro
225                 230                 235                 240

Leu Lys Ile Ile Asp Gly Ala Thr Pro Glu Leu Pro Ala Gly Ala Thr
                245                 250                 255

Ile Gln Glu Val Asp Gly Arg Tyr Tyr Pro Leu Gly Ala Ala Ala
                260                 265                 270

Gln Leu Ile Gly Tyr Val Gly Asp Ile Thr Ala Glu Asp Ile Asp Lys
            275                 280                 285

Asn Pro Glu Leu Ser Ser Asn Gly Lys Ile Gly Arg Ser Gly Leu Glu
290                 295                 300

Met Ala Phe Asp Lys Asp Leu Arg Gly Thr Thr Gly Lys Leu Ser
305                 310                 315                 320

Ile Thr Asp Ala Asp Gly Val Glu Lys Val Leu Ile Glu His Glu
                325                 330                 335

Val Gln Asn Gly Lys Asp Ile Lys Leu Thr Ile Asp Ala Lys Ala Gln
                340                 345                 350

Lys Thr Ala Phe Asp Ser Leu Gly Gly Lys Ala Gly Ser Thr Val Ala
            355                 360                 365

Thr Thr Pro Lys Thr Gly Asp Leu Leu Ala Leu Ala Ser Ser Pro Ser
            370                 375                 380

Tyr Asp Pro Asn Lys Met Thr Asn Gly Ile Ser Gln Glu Asp Tyr Lys
385                 390                 395                 400

Ala Tyr Glu Glu Asn Pro Glu Gln Pro Phe Ile Ser Arg Phe Ala Thr
                405                 410                 415

Gly Tyr Ala Pro Gly Ser Thr Phe Lys Met Ile Thr Ala Ala Ile Gly
                420                 425                 430

Leu Asp Asn Gly Thr Ile Asp Pro Asn Glu Val Leu Thr Ile Asn Gly
            435                 440                 445

Leu Lys Trp Gln Lys Asp Ser Ser Trp Gly Ser Tyr Lys Val Thr Arg
450                 455                 460
```

```
Val Ser Asp Val Ser Gln Val Asp Leu Lys Thr Ala Leu Ile Tyr Ser
465                 470                 475                 480

Asp Asn Ile Tyr Ala Ala Gln Glu Thr Leu Lys Met Gly Glu Lys Lys
            485                 490                 495

Phe Arg Thr Gly Leu Asp Lys Phe Ile Phe Gly Glu Asp Leu Asp Leu
            500                 505                 510

Pro Ile Ser Met Asn Pro Ala Gln Ile Ser Asn Glu Asp Ser Phe Asn
            515                 520                 525

Ser Asp Ile Leu Leu Ala Asp Thr Gly Tyr Gly Gln Gly Glu Leu Leu
            530                 535                 540

Ile Asn Pro Ile Gln Gln Ala Ala Met Tyr Ser Val Phe Ala Asn Asn
545                 550                 555                 560

Gly Thr Leu Val Tyr Pro Lys Leu Ile Ala Asp Lys Glu Thr Lys Asp
                565                 570                 575

Lys Lys Asn Val Ile Gly Glu Thr Ala Leu Gln Thr Ile Val Pro Asp
            580                 585                 590

Leu Arg Glu Val Val Gln Asp Val Asn Gly Thr Ala His Ser Leu Ser
            595                 600                 605

Ala Leu Gly Ile Pro Leu Ala Ala Lys Thr Gly Thr Ala Glu Ile Lys
610                 615                 620

Glu Lys Gln Asp Val Lys Gly Lys Glu Asn Ser Phe Leu Phe Ala Phe
625                 630                 635                 640

Asn Pro Asp Asn Gln Gly Tyr Met Met Val Ser Met Leu Glu Asn Lys
            645                 650                 655

Glu Asp Asp Ser Ala Thr Lys Arg Ala Ser Glu Leu Leu Gln Tyr
            660                 665                 670

Leu Asn Gln Asn Tyr Gln
        675
```

<210> SEQ ID NO 2
<211> LENGTH: 360
<212> TYPE: PRT
<213> ORGANISM: Enterococcus faecium

<400> SEQUENCE: 2

```
Met Lys Lys Ala Lys Leu Phe Gly Leu Gly Ala Val Ala Leu Ala Ala
1               5                   10                  15

Gly Leu Phe Leu Gly Ala Cys Gly Asn Asn Gly Ser Thr Asp Ser Ser
            20                  25                  30

Gly Gly Lys Ser Ser Ser Asp Thr Thr Thr Ala Ala Leu Ile Thr Asp
        35                  40                  45

Thr Gly Gly Val Asp Asp Arg Ser Phe Asn Gln Ser Ala Trp Glu Gly
    50                  55                  60

Leu Glu Lys Trp Gly Lys Asp Gln Gly Leu Ser Arg Gly Asn Asp Gly
65                  70                  75                  80

Phe Gln Tyr Phe Gln Ser Ser Asn Glu Ser Asp Tyr Ile Pro Asn Ile
                85                  90                  95

Asp Gln Ala Leu Asn Ala Gly Phe Lys Thr Ile Phe Gly Ile Gly Tyr
            100                 105                 110

Lys Leu Lys Pro Ala Ile Gln Glu Gln Ala Thr Asn Thr Gly Thr
        115                 120                 125

Asn Phe Val Ile Ile Asp Asp Val Ile Asp Gly Leu Asp Asn Val Val
    130                 135                 140

Ser Ala Thr Phe Lys Asp Asn Glu Ala Ser Tyr Leu Ala Gly Val Ala
```

```
                 145                 150                 155                 160
Ala Ala Tyr Thr Thr Glu Thr Asn Val Val Gly Phe Ile Gly Gly Val
                165                 170                 175

Lys Gly Glu Val Ile Asp Arg Phe Asp Ala Gly Phe Lys Ala Gly Val
                180                 185                 190

Asp Ala Gly Ala Lys Glu Leu Gly Lys Glu Ile Lys Val Leu Asn Gln
                195                 200                 205

Tyr Ala Gly Asp Phe Ser Ala Pro Asp Lys Gly Arg Ser Ile Ala Gln
                210                 215                 220

Gly Met Tyr Ala Gln Asn Ala Asp Ile Ile Phe His Ala Ser Gly Gly
225                 230                 235                 240

Thr Gly Asn Gly Val Phe Gln Glu Ala Lys Ser Leu Asn Glu Ser Gly
                245                 250                 255

Asp Lys Lys Val Trp Val Ile Gly Val Asp Arg Asp Gln Ser Asp Glu
                260                 265                 270

Gly Glu Tyr Thr Leu Asn Gly Glu Lys Lys Asn Phe Thr Leu Thr Ser
                275                 280                 285

Thr Leu Lys Ala Val Gly Thr Val Val Glu Asp Leu Ala Gln Lys Ser
290                 295                 300

Ala Asp Gly Lys Phe Pro Gly Gly Glu His Thr Val Tyr Gly Leu Lys
305                 310                 315                 320

Glu Asp Gly Val Gly Leu Thr Glu Gly Gln Leu Ser Asp Glu Ala Lys
                325                 330                 335

Lys Ala Val Asp Glu Ala Lys Leu Lys Ile Ile Ser Gly Asp Val Lys
                340                 345                 350

Val Pro Glu Thr Pro Glu Glu Asn
                355                 360
```

<210> SEQ ID NO 3
<211> LENGTH: 197
<212> TYPE: PRT
<213> ORGANISM: Enterococcus faecium

<400> SEQUENCE: 3

```
Met Asn Ser Phe Lys Lys Ile Val Leu Gly Thr Thr Phe Ala Ala Gly
1               5                   10                  15

Ala Thr Ala Met Phe Val Gly Thr Thr Asn Ala His Ala Asp Glu Val
                20                  25                  30

Tyr Thr Val Lys Ser Gly Asp Ser Leu Ser Lys Ile Ser Gln Lys Phe
                35                  40                  45

Ala Gly Asp Asn Ser Met Ile Asp Ala Ile Ala Glu Lys Asn Ser Ile
            50                  55                  60

Ala Asn Ile Asn Arg Ile Tyr Val Gly Glu Gln Leu Thr Ile Pro Thr
65                  70                  75                  80

Ser Asn Asp Ser Ser Ala Thr Thr Glu Asn Thr Ala Ser Thr Thr Glu
                85                  90                  95

Thr Ala Thr Gln Glu His Thr Tyr Val Ala Pro Val Glu Thr Val Glu
                100                 105                 110

Val Ala Pro Ala Ala Pro Ala Ala Ala Thr Ala Pro Thr Ser Ser Ser
            115                 120                 125

Ala Lys Glu Trp Ile Ala Gln Lys Glu Ser Gly Gly Ser Tyr Thr Ala
        130                 135                 140

Thr Asn Gly Arg Tyr Ile Gly Arg Tyr Gln Leu Asp Ala Ser Tyr Leu
145                 150                 155                 160
```

```
Asn Gly Asp Tyr Ser Ala Ala Asn Gln Glu Arg Val Ala Glu Gln Tyr
                165                 170                 175

Val Thr Ser Arg Tyr Gly Ser Trp Asp Ala Ala Lys Thr Phe Trp Leu
            180                 185                 190

Ala Asn Gly Trp Tyr
        195

<210> SEQ ID NO 4
<211> LENGTH: 435
<212> TYPE: PRT
<213> ORGANISM: Enterococcus faecium

<400> SEQUENCE: 4

Met Ser Ile Lys Lys Thr Arg Leu Val Leu Leu Ala Ser Leu Ile
1               5                   10                  15

Leu Cys Leu Ala Ser Phe Leu Pro Ala Val Ala Val Gln Ala Glu Asp
            20                  25                  30

Thr Phe Lys Val Asn Ala Lys Ala Phe Ala Val Asp Ala Gln Ser
        35                  40                  45

Gly Lys Ile Leu Tyr Asp Gln Asp Gly Glu Lys Thr Met Gly Ile Ala
    50                  55                  60

Ser Ile Thr Lys Ile Ile Gly Leu Tyr Ile Val Leu Asp Gln Val Lys
65                  70                  75                  80

Glu Gly Lys Leu Ser Trp Asp Asp Lys Val Ser Ile Ser Asp Tyr Ala
                85                  90                  95

Glu Asn Leu Ser Ile Thr Pro Asp Leu Ser Asn Val Pro Leu His Lys
            100                 105                 110

Glu Asn Thr Tyr Thr Val Lys Glu Leu Phe Asp Ser Ala Ile Ile Gln
        115                 120                 125

Ser Ala Asn Ala Ser Met Val Ala Leu Ala Glu Lys Ile Ser Gly Ser
    130                 135                 140

Glu Ala Lys Phe Thr Glu Arg Met Lys Glu Gln Leu Lys Asp Trp Gly
145                 150                 155                 160

Ile Lys Asp Ala Thr Ile Val Asn Ala Ser Gly Leu Asn Asn Ser Tyr
                165                 170                 175

Leu Gly Glu Asn Arg Pro Glu Gly Thr Val Glu Asn Asp Glu Asn Gln
            180                 185                 190

Met Ser Ala Gln Asp Val Ala Ile Val Ala Arg His Leu Ile Leu Asp
        195                 200                 205

Phe Pro Glu Ile Leu Asp Val Ser Ser Thr Thr Gln Met Phe Gly
    210                 215                 220

Glu Asn Thr Gln Ser Pro Val Glu Met Val Asn Trp Asn Trp Met Leu
225                 230                 235                 240

Pro Gly Phe Val Asn Tyr Lys Glu Gly Val Asp Gly Leu Lys Thr Gly
                245                 250                 255

Thr Thr Glu Leu Ala Gly Ala Cys Phe Val Gly Thr Ile Thr Lys Asn
            260                 265                 270

Asp Gln Arg Ile Ile Thr Val Val Leu Asn Ala Asp Gly His Ala Glu
        275                 280                 285

Asn Pro Ser Ala Arg Phe Asn Glu Thr Asp Arg Leu Met Asp Tyr Cys
    290                 295                 300

Tyr Asp Asn Trp Ser Glu Lys Glu Leu Gly Lys Ala Asn Ala Ser Ile
305                 310                 315                 320

Pro Ser Leu Lys Thr Ile Asp Val Lys Asp Gly Lys Glu Ser Thr Val
                325                 330                 335
```

Pro Val Val Leu Lys Ser Pro Val Lys Val Trp Val Arg Asn Asp Met
            340                 345                 350

Asp Thr Gly Lys Leu Thr Ile Thr Pro Thr Leu Asp Lys Lys Gln Val
            355                 360                 365

Thr Asp Asn Glu Ile Gln Ala Pro Met Asp Lys Gly Thr Lys Ile Gly
            370                 375                 380

Thr Ala Thr Ile Thr Leu Ala Asp Asp Lys Leu Gly Tyr Leu Glu Asp
385                 390                 395                 400

Asn Asn Ala Pro Ser Thr Glu Ile Ile Thr Asp Lys Thr Val Glu Lys
                405                 410                 415

Ala Asn Ile Phe Cys Leu Gly Trp Arg Arg Val Ala Glu Phe Phe Gly
            420                 425                 430

Asn Leu Phe
        435

<210> SEQ ID NO 5
<211> LENGTH: 336
<212> TYPE: PRT
<213> ORGANISM: Enterococcus faecium

<400> SEQUENCE: 5

Met Lys Lys Lys Ser Ile Ile Leu Ala Ala Thr Ser Ala Leu Ala Val
1               5                   10                  15

Leu Thr Leu Ala Ala Cys Ser Gly Asp Thr Asn Lys Asp Ile Ala Thr
            20                  25                  30

Met Lys Gly Gly Thr Ile Thr Val Ser Asp Phe Tyr Asp Glu Ala Lys
            35                  40                  45

Leu Glu Ser Ser Asn Gln Ser Leu Val Gln Arg Met Ile Ile Tyr Lys
        50                  55                  60

Val Phe Asn Asn Lys Tyr Gly Asp Lys Val Thr Asp Lys Gln Val Asp
65                  70                  75                  80

Ala Glu Tyr Asp Lys Gln Ala Lys Ser Leu Gly Asp Thr Phe Glu Ser
                85                  90                  95

Gln Leu Glu Thr Ala Gly Tyr Thr Lys Asp Ser Tyr Lys Glu Tyr Ile
            100                 105                 110

Arg Asn Asn Leu Ala Phe Glu Ala Gly Leu Lys Ala His Val Asp Ile
        115                 120                 125

Thr Asp Asp Asp Leu Lys Thr Ala Trp Glu Ser Phe His Pro Glu Val
130                 135                 140

Glu Ala Gln Ile Ile Lys Leu Ser Ser Glu Asp Glu Ala Lys Asp Val
145                 150                 155                 160

Lys Lys Ser Ala Asp Asp Gly Asp Asp Phe Ser Lys Leu Ala Lys Asp
                165                 170                 175

Lys Ser Thr Asp Ser Glu Thr Lys Glu Asp Gly Gly Lys Val Lys Phe
            180                 185                 190

Asp Ser Thr Thr Thr Ile Pro Ala Glu Val Lys Glu Ala Ala Phe
        195                 200                 205

Lys Leu Lys Asp Gly Glu Val Ser Asp Val Ile Thr Ala Thr Asn Thr
    210                 215                 220

Thr Ser Tyr Ala Thr Glu Tyr Tyr Val Val Lys Met Val Lys Asn Gln
225                 230                 235                 240

Asn Lys Gly Asn Asp Met Asp Lys Tyr Lys Asp Gln Leu Lys Glu Ile
                245                 250                 255

Ala Thr Glu Thr Lys Leu Ser Asp Asn Thr Phe Thr Thr Lys Val Ile

```
              260                 265                 270
Gly Glu Glu Leu Lys Asp Ala Asn Val Lys Ile Lys Asp Asp Ala Phe
            275                 280                 285

Glu Asn Val Leu Ser Ala Phe Thr Thr Thr Ser Ser Ser Thr Lys Asp
        290                 295                 300

Ser Ser Glu Ala Thr Ser Ser Thr Lys Ser Ser Asp Thr Lys Ser Thr
305                 310                 315                 320

Asp Ser Thr Lys Glu Ser Ser Thr Glu Glu Thr Thr Asp Ser Ser Lys
                325                 330                 335

<210> SEQ ID NO 6
<211> LENGTH: 432
<212> TYPE: PRT
<213> ORGANISM: Enterococcus faecium

<400> SEQUENCE: 6

Met Ser Ile Ile Thr Asp Val Tyr Ala Arg Glu Ile Leu Asp Ser Arg
1               5                   10                  15

Gly Asn Pro Thr Ile Glu Val Glu Val Tyr Thr Glu Ser Gly Ala Phe
            20                  25                  30

Gly Arg Gly Met Val Pro Ser Gly Ala Ser Thr Gly Glu Tyr Glu Ala
        35                  40                  45

Val Glu Leu Arg Asp Gly Asp Lys Ala Arg Tyr Gly Gly Lys Gly Val
    50                  55                  60

Thr Lys Ala Val Asp Asn Val Asn Asn Ile Ile Ala Glu Ala Ile Ile
65                  70                  75                  80

Gly Tyr Asp Val Arg Asp Gln Met Ala Ile Asp Lys Ala Met Ile Ala
                85                  90                  95

Leu Asp Gly Thr Pro Asn Lys Gly Lys Leu Gly Ala Asn Ala Ile Leu
            100                 105                 110

Gly Val Ser Ile Ala Val Ala Arg Ala Ala Asp Tyr Leu Glu Val
        115                 120                 125

Pro Leu Tyr His Tyr Leu Gly Gly Phe Asn Thr Lys Val Leu Pro Thr
    130                 135                 140

Pro Met Met Asn Ile Ile Asn Gly Gly Ser His Ala Asp Asn Ser Ile
145                 150                 155                 160

Asp Phe Gln Glu Phe Met Ile Met Pro Val Gly Ala Pro Thr Phe Lys
                165                 170                 175

Glu Ala Leu Arg Met Gly Ala Glu Val Phe His Ala Leu Ala Ser Ile
            180                 185                 190

Leu Lys Ala Arg Gly Leu Ala Thr Ser Val Gly Asp Glu Gly Gly Phe
        195                 200                 205

Ala Pro Asn Leu Gly Ser Asn Glu Glu Gly Phe Glu Val Ile Ile Glu
    210                 215                 220

Ala Ile Glu Lys Ala Gly Tyr Val Pro Gly Lys Asp Val Val Leu Ala
225                 230                 235                 240

Met Asp Ala Ala Ser Ser Glu Phe Tyr Asp Lys Glu Lys Gly Val Tyr
                245                 250                 255

Val Leu Ala Asp Ser Gly Glu Gly Glu Lys Thr Thr Asp Glu Met Ile
            260                 265                 270

Lys Phe Tyr Glu Glu Leu Val Ser Lys Tyr Pro Ile Ile Ser Ile Glu
        275                 280                 285

Asp Gly Leu Asp Glu Asn Asp Trp Asp Gly Phe Lys Lys Leu Thr Asp
    290                 295                 300
```

```
Val Leu Gly Asp Lys Val Gln Leu Val Gly Asp Asp Leu Phe Val Thr
305                 310                 315                 320

Asn Thr Gln Lys Leu Ser Glu Gly Ile Glu Lys Gly Ile Ala Asn Ser
            325                 330                 335

Ile Leu Ile Lys Val Asn Gln Ile Gly Thr Leu Thr Glu Thr Phe Glu
            340                 345                 350

Ala Ile Glu Met Ala Lys Glu Ala Gly Tyr Thr Ala Val Val Ser His
            355                 360                 365

Arg Ser Gly Glu Thr Glu Asp Ser Thr Ile Ser Asp Ile Ala Val Ala
    370                 375                 380

Thr Asn Ala Gly Gln Ile Lys Thr Gly Ser Leu Ser Arg Thr Asp Arg
385                 390                 395                 400

Ile Ala Lys Tyr Asn Gln Leu Leu Arg Ile Glu Asp Gln Leu Gly Glu
                405                 410                 415

Val Ala Glu Tyr Lys Gly Leu Lys Ser Phe Tyr Asn Leu Lys Asn Lys
                420                 425                 430
```

<210> SEQ ID NO 7
<211> LENGTH: 685
<212> TYPE: PRT
<213> ORGANISM: Enterococcus faecium

<400> SEQUENCE: 7

```
Met Lys Leu Phe Asn Pro Lys Thr Val Leu Ala Ile Gly Thr Phe Ala
1               5                   10                  15

Ala Ser Leu Ser Leu Ala Gly Ser Val Asp Ala Ala Ser Thr Asn Val
            20                  25                  30

Met Tyr Arg Leu Tyr Asn Pro Asn Asn Glu His Phe Tyr Thr Ser
        35                  40                  45

Ser Lys Lys Glu Arg Asp His Leu Val Lys Ile Lys Trp Gly Asn Tyr
    50                  55                  60

Glu Gly Pro Ala Trp Glu Ala Pro Thr Ser Gly Gly His Leu Val Tyr
65                  70                  75                  80

Arg Leu Tyr Asn Lys Gly Leu Arg Asp His His Tyr Thr Ala Ser Trp
                85                  90                  95

Asp Glu Val Lys Trp Leu Thr Lys Asn Tyr Gly Trp Thr Tyr Glu Gly
            100                 105                 110

Pro Ala Trp Arg Ser Ala Glu Lys Asn Asn Lys Pro Ile Tyr Arg Leu
        115                 120                 125

Phe Leu Pro Gly Val Lys Ser Gly Ser His His Tyr Thr Ala Ser Trp
130                 135                 140

Lys Glu Val Gln Trp Leu Thr Lys Asp Tyr Gly Trp Lys Tyr Glu Gly
145                 150                 155                 160

Ile Gly Trp Tyr Gly Ala Asp Thr Ser Lys Pro Lys Val Asn Lys Ser
                165                 170                 175

Ala Leu Glu Ala Leu Tyr Thr Ser Val Lys Gly Thr Lys Lys Gly Asp
            180                 185                 190

Tyr Thr Asp Asn Thr Trp Asn Ala Phe Gln Thr Ala Leu Asn Asn Ala
        195                 200                 205

Lys Lys Val Leu Asn Asp Ser Lys Ala Thr Gln Lys Gln Val Asp Ser
    210                 215                 220

Ala Lys Asn Lys Leu Asp Ser Ala Tyr Lys Gly Leu Lys Lys Lys Pro
225                 230                 235                 240

Val Pro Thr Val Asn Lys Ala Glu Leu Gln Ala Leu Tyr Asn Arg Val
                245                 250                 255
```

-continued

```
Lys Ser Thr Ala Lys Gly Asp Phe Thr Glu Glu Ser Trp Asn Asn Phe
            260                 265                 270
Gln Thr Ala Leu Ser Asn Ala Lys Val Leu Asp Ser Lys Ala
        275                 280                 285
Ser Gln Ala Gln Val Asn Asn Ala Lys Asn Ser Leu Asp Ala Ala Phe
    290                 295                 300
Lys Gly Leu Gln His Lys Pro Glu Thr Pro Lys Glu Tyr Met Val Thr
305                 310                 315                 320
Ile Asn His Ile Asp Asn Gln Thr Gly Gln Val Ile Ala Thr Asp Gln
                325                 330                 335
Ala Lys Val Thr Ser Gly Ser Thr Tyr Thr Ala Lys Ala Lys Ala Phe
            340                 345                 350
Lys Tyr Ser Glu Gly Ala Lys Asp Asn Phe Ser Tyr Lys Val Ile Gly
        355                 360                 365
Asn Asp Thr Gln Ser Lys Thr Ile Thr Gly Asn Thr Ile Thr Phe
    370                 375                 380
Asn Tyr Asn Gln Val His Gln Ile Asn Leu Leu Cys Asn Asn Asn Tyr
385                 390                 395                 400
Lys Asn Glu Gly Arg Val Asn Ile Leu Lys Glu Gln Ile Val Asn Val
                405                 410                 415
Thr His Gly Asp Ser Val Thr Leu Thr Ala Pro Ser Ile Gln Gly Tyr
            420                 425                 430
Val Leu Asp Asp Arg Val Glu Pro Thr Asn Ser Val Thr Leu Asn Asn
        435                 440                 445
Val Thr Glu Ser Gln Asn Tyr Ile Phe Asn Tyr Thr Arg Lys Phe Asn
    450                 455                 460
Val Thr Val Asn His Val Asn Ala Asp Thr Asn Ala Val Leu Ser Ser
465                 470                 475                 480
Glu Ser Lys Thr Val Tyr Glu Gly Asp Ser Phe Ala Thr Pro Trp Lys
                485                 490                 495
Asn Met Thr Asp Gln Asn Tyr Phe Leu Cys Arg Asn Asp Asp Pro Thr
            500                 505                 510
Val Thr Val Asp Lys Asn Gly Gln Arg Ser Ile Asn Asn Val Asp Gln
        515                 520                 525
Asn Lys Thr Ile Thr Phe Lys Tyr Lys Lys Ile Ser Leu Asp Glu Leu
    530                 535                 540
Arg Asn Phe Met Arg Gln Lys Glu Leu Ala Trp Leu Asn Asp Tyr Arg
545                 550                 555                 560
Gln Gln Asn Gly Val Ala Pro Met Gln Phe Asn Asp Ile Val Gln Gln
                565                 570                 575
Ala Ala Asp Ile Arg Ala Lys Glu Leu Gln Val Ser Phe Ser His Tyr
            580                 585                 590
Arg Pro Gly Gly Gly Thr Phe Gln Asp Leu Leu Glu Ser Leu Gly Cys
        595                 600                 605
Tyr Gly Ala Lys Gly Glu Asn Ile Ser Gln Thr Gly Leu Tyr Ile Asp
    610                 615                 620
Asp Leu Leu Ser Asp Asp Gly Ala Ile Asp Ala Met Val Gly Trp Lys
625                 630                 635                 640
Asn Ser Pro Ala His Asn Ala Asn Leu Leu Tyr Asn Asn Gln Ser Ile
                645                 650                 655
Leu Gly Leu Gly His Asn Phe Val Val Asp Ser Ala Gly Arg Ile Gly
            660                 665                 670
```

```
Val Asp Asn Val Phe Ile Ser Ala Asn Pro Ile Phe Lys
        675                 680                 685
```

<210> SEQ ID NO 8
<211> LENGTH: 228
<212> TYPE: PRT
<213> ORGANISM: Enterococcus faecium

<400> SEQUENCE: 8

```
Met Asn Pro Leu Glu Ser Leu Thr Lys Glu Gln Met Asp Asn Gly Glu
1               5                   10                  15

Asp Tyr Val Ser Val Met Glu Asp Asn Leu Lys Ala Leu Glu Lys Thr
            20                  25                  30

Thr Met Val Ala Gly Glu Val Pro Glu Lys Glu Ala Lys Asp
        35                  40                  45

Glu Lys Thr Val Ala Asn Gly Tyr Phe Lys Asp Ala Val Lys Asp
    50                  55                  60

Arg Glu Leu Ser Asp Tyr Thr Gly Glu Trp Gln Ser Val Tyr Pro Leu
65                  70                  75                  80

Leu Lys Asp Gly Ile Leu Asp Glu Val Phe Asp Tyr Lys Ala Lys Leu
                85                  90                  95

Asn Lys Asp Met Thr Ala Ala Glu Tyr Lys Asp Tyr Tyr Thr Thr Gly
            100                 105                 110

Tyr Lys Thr Asp Ile Asp Thr Ile Asn Ile Lys Asp Asn Thr Ile Asp
        115                 120                 125

Phe Val Val Asn Gly Glu His His Gln Tyr Thr Tyr Lys Tyr Val Gly
    130                 135                 140

Tyr Lys Ile Leu Asn Tyr Glu Lys Gly Asn Arg Gly Val Arg Phe Asn
145                 150                 155                 160

Phe Glu Thr Asp Asp Ala Gly Ala Gly Arg Phe Lys Tyr Ile Gln Phe
                165                 170                 175

Ser Asp His Gly Ile Ala Pro Ser Lys Ala Glu His Phe His Ile Phe
            180                 185                 190

Phe Gly Gly Glu Ser Gln Glu Lys Leu Tyr Asn Glu Met His Asn Trp
        195                 200                 205

Pro Thr Phe Tyr Pro Ala Ser Leu Ser Glu His Glu Ile Ala Gln Glu
    210                 215                 220

Met Met Ala His
225
```

<210> SEQ ID NO 9
<211> LENGTH: 237
<212> TYPE: PRT
<213> ORGANISM: Enterococcus faecium

<400> SEQUENCE: 9

```
Met Lys Lys Lys Gly Lys Ala Lys Arg Trp Leu Val Asn Ile Leu Leu
1               5                   10                  15

Phe Leu Leu Leu Leu Val Gly Leu Ala Leu Ile Phe Asn Glu Gln Ile
            20                  25                  30

Lys Asp Tyr Phe Val Arg Glu Thr Gly Asp Lys Tyr Ala Ile Ala Asn
        35                  40                  45

Val Thr Lys Glu Asp Leu Lys Lys Asn Asn Asp Lys Asp Val Ser Phe
    50                  55                  60

Asp Phe Asp Ala Val Glu Pro Met Thr Thr Glu Gly Val Met Arg Ser
65                  70                  75                  80
```

```
Gln Met Arg Gly Thr Asp Leu Pro Val Ile Ala Ser Ile Ala Val Pro
                85                  90                  95

Ser Val Ser Ile Asn Leu Pro Val Phe Lys Gly Leu Asp Asn Thr Ser
            100                 105                 110

Leu Leu Tyr Gly Ala Gly Thr Leu Ser Pro Asp Gln Glu Met Gly Lys
        115                 120                 125

Gly Asn Tyr Ala Leu Ala Ser His Arg Ala Thr Asn Pro Glu Leu Leu
    130                 135                 140

Phe Thr Pro Leu Glu Asn Leu Glu Met Gly Ala Lys Ile Tyr Leu Thr
145                 150                 155                 160

Asp Leu Glu Asn Val Tyr Thr Tyr Lys Thr Phe Phe Lys Glu Lys Val
                165                 170                 175

Ala Pro Thr Asp Thr Gln Leu Leu Asn Glu Val Glu Gly Lys Glu Ile
            180                 185                 190

Val Thr Leu Ile Thr Cys Gly Asp Met Asp Ala Val Thr Arg Leu Val
        195                 200                 205

Val Gln Gly Glu Leu Glu Ser Val Thr Ser Ile Lys Asp Ala Thr Asp
    210                 215                 220

Asp Met Arg Ser Ala Phe Asn Leu Glu Thr Lys Thr Phe
225                 230                 235

<210> SEQ ID NO 10
<211> LENGTH: 13
<212> TYPE: PRT
<213> ORGANISM: Enterococcus faecium

<400> SEQUENCE: 10

Lys Leu Lys Val Val Thr Asn Ser Ile Leu Ala Asp
1               5                   10

<210> SEQ ID NO 11
<211> LENGTH: 12
<212> TYPE: PRT
<213> ORGANISM: Enterococcus faecium

<400> SEQUENCE: 11

Lys Ile Asp Leu His Ser Ile Val Pro Ile Gly Lys
1               5                   10

<210> SEQ ID NO 12
<211> LENGTH: 12
<212> TYPE: PRT
<213> ORGANISM: Enterococcus faecium

<400> SEQUENCE: 12

Thr Thr Lys Val Pro Ser Leu Phe Val Glu Ser Ser
1               5                   10

<210> SEQ ID NO 13
<211> LENGTH: 9
<212> TYPE: PRT
<213> ORGANISM: Enterococcus faecium

<400> SEQUENCE: 13

Gly Ile Asp Val Ile Tyr Leu Glu Gly
1               5

<210> SEQ ID NO 14
<211> LENGTH: 23
<212> TYPE: PRT
<213> ORGANISM: Enterococcus faecium
```

```
<400> SEQUENCE: 14

Ile Val Thr Ser Glu Gly Cys Phe Lys Tyr Phe Ser Lys Ala Tyr Asn
1               5                   10                  15

Val Pro Ser Ala Tyr Ile Trp
            20

<210> SEQ ID NO 15
<211> LENGTH: 9
<212> TYPE: PRT
<213> ORGANISM: Enterococcus faecium

<400> SEQUENCE: 15

Gln Ile Lys His Leu Val Glu Lys Leu
1               5

<210> SEQ ID NO 16
<211> LENGTH: 9
<212> TYPE: PRT
<213> ORGANISM: Enterococcus faecium

<400> SEQUENCE: 16

Ala Asp Leu Ile Phe Tyr Asn Gly Val
1               5

<210> SEQ ID NO 17
<211> LENGTH: 7
<212> TYPE: PRT
<213> ORGANISM: Enterococcus faecium

<400> SEQUENCE: 17

Ile Pro Ile Tyr Ser Thr Ile
1               5

<210> SEQ ID NO 18
<211> LENGTH: 6
<212> TYPE: PRT
<213> ORGANISM: Enterococcus faecium

<400> SEQUENCE: 18

Thr Lys Leu Val Lys Asn
1               5

<210> SEQ ID NO 19
<211> LENGTH: 8
<212> TYPE: PRT
<213> ORGANISM: Enterococcus faecium

<400> SEQUENCE: 19

Tyr Glu Pro Leu Pro Glu Asp Val
1               5

<210> SEQ ID NO 20
<211> LENGTH: 6
<212> TYPE: PRT
<213> ORGANISM: Enterococcus faecium

<400> SEQUENCE: 20

Gly Ile Ile Tyr Ala Lys
1               5

<210> SEQ ID NO 21
<211> LENGTH: 8
<212> TYPE: PRT
```

<213> ORGANISM: Enterococcus faecium

<400> SEQUENCE: 21

Tyr Ile Glu Lys Leu Asp Ser Leu
1               5

<210> SEQ ID NO 22
<211> LENGTH: 10
<212> TYPE: PRT
<213> ORGANISM: Enterococcus faecium

<400> SEQUENCE: 22

Gln Ser Val Tyr Pro Leu Leu Lys Asp Gly
1               5                   10

<210> SEQ ID NO 23
<211> LENGTH: 8
<212> TYPE: PRT
<213> ORGANISM: Enterococcus faecium

<400> SEQUENCE: 23

Asp Ala Asp Val Phe Val Tyr His
1               5

<210> SEQ ID NO 24
<211> LENGTH: 17
<212> TYPE: PRT
<213> ORGANISM: Enterococcus faecium

<400> SEQUENCE: 24

Ile Lys Asp Gln Leu Val Lys Leu Tyr Pro Lys Lys Ala Lys Val Phe
1               5                   10                  15

Glu

<210> SEQ ID NO 25
<211> LENGTH: 14
<212> TYPE: PRT
<213> ORGANISM: Enterococcus faecium

<400> SEQUENCE: 25

His Gln Tyr Thr Tyr Lys Tyr Val Gly Tyr Lys Ile Leu Asn
1               5                   10

<210> SEQ ID NO 26
<211> LENGTH: 27
<212> TYPE: PRT
<213> ORGANISM: Enterococcus faecium

<400> SEQUENCE: 26

Lys Ser Phe Val Thr Gln His Ala Ala Phe Gly Tyr Leu Ala Leu Asp
1               5                   10                  15

Tyr Gly Leu Lys Gln Val Pro Ile Ala Gly Leu
            20                  25

<210> SEQ ID NO 27
<211> LENGTH: 10
<212> TYPE: PRT
<213> ORGANISM: Enterococcus faecium

<400> SEQUENCE: 27

Asn Val Asp Leu Met Val Pro Ala Gly Ser
1               5                   10

```
<210> SEQ ID NO 28
<211> LENGTH: 11
<212> TYPE: PRT
<213> ORGANISM: Enterococcus faecium

<400> SEQUENCE: 28

Lys Leu Glu Val Leu Asn Pro Leu Glu Ser Leu
1               5                   10

<210> SEQ ID NO 29
<211> LENGTH: 8
<212> TYPE: PRT
<213> ORGANISM: Enterococcus faecium

<400> SEQUENCE: 29

Gly Glu Glu Val Val Pro Glu Lys
1               5

<210> SEQ ID NO 30
<211> LENGTH: 11
<212> TYPE: PRT
<213> ORGANISM: Enterococcus faecium

<400> SEQUENCE: 30

Leu Glu Ile Val Thr Thr Phe Tyr Pro Met Tyr
1               5                   10

<210> SEQ ID NO 31
<211> LENGTH: 10
<212> TYPE: PRT
<213> ORGANISM: Enterococcus faecium

<400> SEQUENCE: 31

Phe Tyr Pro Ala Ser Leu Ser Lys His Glu
1               5                   10

<210> SEQ ID NO 32
<211> LENGTH: 8
<212> TYPE: PRT
<213> ORGANISM: Enterococcus faecium

<400> SEQUENCE: 32

Ile Asp Phe Val Val Asn Gly Glu
1               5

<210> SEQ ID NO 33
<211> LENGTH: 23
<212> TYPE: PRT
<213> ORGANISM: Enterococcus faecium

<400> SEQUENCE: 33

Phe Lys Tyr Ile Gln Phe Ser Asp His Gly Ile Ala Pro Ser Lys Ala
1               5                   10                  15

Glu His Phe His Ile Phe Phe
            20

<210> SEQ ID NO 34
<211> LENGTH: 7
<212> TYPE: PRT
<213> ORGANISM: Enterococcus faecium

<400> SEQUENCE: 34

Leu Ala Glu Leu Lys Glu Tyr
1               5
```

```
<210> SEQ ID NO 35
<211> LENGTH: 7
<212> TYPE: PRT
<213> ORGANISM: Enterococcus faecium

<400> SEQUENCE: 35

Gly Pro Asn Val Val Glu Gly
1               5

<210> SEQ ID NO 36
<211> LENGTH: 7
<212> TYPE: PRT
<213> ORGANISM: Enterococcus faecium

<400> SEQUENCE: 36

His Thr Trp Val Ser Pro Lys
1               5

<210> SEQ ID NO 37
<211> LENGTH: 8
<212> TYPE: PRT
<213> ORGANISM: Enterococcus faecium

<400> SEQUENCE: 37

Leu Asp Glu Val Phe Asp Tyr Lys
1               5

<210> SEQ ID NO 38
<211> LENGTH: 6
<212> TYPE: PRT
<213> ORGANISM: Enterococcus faecium

<400> SEQUENCE: 38

Met Ile Leu Leu Pro Gly
1               5

<210> SEQ ID NO 39
<211> LENGTH: 6
<212> TYPE: PRT
<213> ORGANISM: Enterococcus faecium

<400> SEQUENCE: 39

Asn Tyr Ile Tyr Phe Glu
1               5

<210> SEQ ID NO 40
<211> LENGTH: 9
<212> TYPE: PRT
<213> ORGANISM: Enterococcus faecium

<400> SEQUENCE: 40

Tyr Leu Thr Lys Leu Lys Arg Leu Asp
1               5

<210> SEQ ID NO 41
<211> LENGTH: 11
<212> TYPE: PRT
<213> ORGANISM: Enterococcus faecium

<400> SEQUENCE: 41

Gly Thr Leu Val Tyr Pro Lys Leu Ile Ala Asp
1               5                   10

<210> SEQ ID NO 42
```

```
<211> LENGTH: 12
<212> TYPE: PRT
<213> ORGANISM: Enterococcus faecium

<400> SEQUENCE: 42

Ala Tyr Ile Ala Gly Ala Val Ile Leu Ile Ala Ala
1               5                   10

<210> SEQ ID NO 43
<211> LENGTH: 10
<212> TYPE: PRT
<213> ORGANISM: Enterococcus faecium

<400> SEQUENCE: 43

Leu Lys Gln Leu Gly Val Val Pro Ser Lys
1               5                   10

<210> SEQ ID NO 44
<211> LENGTH: 24
<212> TYPE: PRT
<213> ORGANISM: Enterococcus faecium

<400> SEQUENCE: 44

Ser Tyr Gln Val Thr Arg Val Ser Asp Val Ser Gln Val Asp Leu Lys
1               5                   10                  15

Thr Ala Leu Ile Tyr Ser Asp Asn
            20

<210> SEQ ID NO 45
<211> LENGTH: 20
<212> TYPE: PRT
<213> ORGANISM: Enterococcus faecium

<400> SEQUENCE: 45

Asn Gln Ala Ile Ser Gln Ser Trp Val Gln Pro Asp Tyr Phe Val Pro
1               5                   10                  15

Leu Lys Ile Ile
            20

<210> SEQ ID NO 46
<211> LENGTH: 9
<212> TYPE: PRT
<213> ORGANISM: Enterococcus faecium

<400> SEQUENCE: 46

Glu Lys Lys Val Leu Ile Glu His Glu
1               5

<210> SEQ ID NO 47
<211> LENGTH: 11
<212> TYPE: PRT
<213> ORGANISM: Enterococcus faecium

<400> SEQUENCE: 47

Gly Asp Leu Leu Ala Leu Ala Ser Ser Pro Ser
1               5                   10

<210> SEQ ID NO 48
<211> LENGTH: 25
<212> TYPE: PRT
<213> ORGANISM: Enterococcus faecium

<400> SEQUENCE: 48

Ile Gln Glu Val Asp Gly Arg Tyr Tyr Pro Leu Gly Glu Ala Ala Ala
```

```
1               5                   10                  15
Gln Leu Ile Gly Tyr Val Gly Asp Ile
            20                  25

<210> SEQ ID NO 49
<211> LENGTH: 17
<212> TYPE: PRT
<213> ORGANISM: Enterococcus faecium

<400> SEQUENCE: 49

Gly Gly Tyr Phe Tyr Tyr Gln His Tyr Gln Glu Thr Gln Ala Val Glu
1               5                   10                  15

Ala

<210> SEQ ID NO 50
<211> LENGTH: 15
<212> TYPE: PRT
<213> ORGANISM: Enterococcus faecium

<400> SEQUENCE: 50

Leu Gln Thr Ile Val Pro Asp Leu Arg Glu Val Val Gln Asp Val
1               5                   10                  15

<210> SEQ ID NO 51
<211> LENGTH: 8
<212> TYPE: PRT
<213> ORGANISM: Enterococcus faecium

<400> SEQUENCE: 51

Val Glu Gln Phe Val Gln Ala Leu
1               5

<210> SEQ ID NO 52
<211> LENGTH: 9
<212> TYPE: PRT
<213> ORGANISM: Enterococcus faecium

<400> SEQUENCE: 52

Ser Glu Leu Leu Gln Tyr Leu Asn Gln
1               5

<210> SEQ ID NO 53
<211> LENGTH: 13
<212> TYPE: PRT
<213> ORGANISM: Enterococcus faecium

<400> SEQUENCE: 53

His Ser Leu Ser Ala Leu Gly Ile Pro Leu Ala Ala Lys
1               5                   10

<210> SEQ ID NO 54
<211> LENGTH: 17
<212> TYPE: PRT
<213> ORGANISM: Enterococcus faecium

<400> SEQUENCE: 54

Gly Glu Leu Leu Ile Asn Pro Ile Gln Gln Ala Ala Met Tyr Ser Val
1               5                   10                  15

Phe

<210> SEQ ID NO 55
<211> LENGTH: 6
<212> TYPE: PRT
```

<213> ORGANISM: Enterococcus faecium

<400> SEQUENCE: 55

Pro Asn Leu Val Phe Pro
1               5

<210> SEQ ID NO 56
<211> LENGTH: 15
<212> TYPE: PRT
<213> ORGANISM: Enterococcus faecium

<400> SEQUENCE: 56

Ala Ala Asp Val Lys Gly Leu Gln Ile Ser Asn Leu Lys Val Asp
1               5                   10                  15

<210> SEQ ID NO 57
<211> LENGTH: 8
<212> TYPE: PRT
<213> ORGANISM: Enterococcus faecium

<400> SEQUENCE: 57

Pro Asn Glu Val Leu Thr Ile Asn
1               5

<210> SEQ ID NO 58
<211> LENGTH: 6
<212> TYPE: PRT
<213> ORGANISM: Enterococcus faecium

<400> SEQUENCE: 58

Ile Thr Ala Ala Ile Gly
1               5

<210> SEQ ID NO 59
<211> LENGTH: 7
<212> TYPE: PRT
<213> ORGANISM: Enterococcus faecium

<400> SEQUENCE: 59

Ser Asp Ile Leu Leu Ala Asp
1               5

<210> SEQ ID NO 60
<211> LENGTH: 8
<212> TYPE: PRT
<213> ORGANISM: Enterococcus faecium

<400> SEQUENCE: 60

Ile Lys Ala Ile Ala Ser Ser Phe
1               5

<210> SEQ ID NO 61
<211> LENGTH: 6
<212> TYPE: PRT
<213> ORGANISM: Enterococcus faecium

<400> SEQUENCE: 61

Tyr Ser Phe Ser Tyr Lys
1               5

<210> SEQ ID NO 62
<211> LENGTH: 6
<212> TYPE: PRT
<213> ORGANISM: Enterococcus faecium

```
<400> SEQUENCE: 62

Ser Phe Leu Phe Ala Phe
1               5

<210> SEQ ID NO 63
<211> LENGTH: 7
<212> TYPE: PRT
<213> ORGANISM: Enterococcus faecium

<400> SEQUENCE: 63

Lys Val Ser Leu Thr Thr Gln
1               5

<210> SEQ ID NO 64
<211> LENGTH: 10
<212> TYPE: PRT
<213> ORGANISM: Enterococcus faecium

<400> SEQUENCE: 64

Gly Glu Leu Lys Asp Leu Ser Tyr Lys Gly
1               5                   10

<210> SEQ ID NO 65
<211> LENGTH: 7
<212> TYPE: PRT
<213> ORGANISM: Enterococcus faecium

<400> SEQUENCE: 65

Pro Glu Leu Pro Ala Gly Ala
1               5

<210> SEQ ID NO 66
<211> LENGTH: 6
<212> TYPE: PRT
<213> ORGANISM: Enterococcus faecium

<400> SEQUENCE: 66

Gln Pro Phe Ile Ser Arg
1               5

<210> SEQ ID NO 67
<211> LENGTH: 7
<212> TYPE: PRT
<213> ORGANISM: Enterococcus faecium

<400> SEQUENCE: 67

Gly Ser Thr Val Ala Thr Thr
1               5

<210> SEQ ID NO 68
<211> LENGTH: 8
<212> TYPE: PRT
<213> ORGANISM: Enterococcus faecium

<400> SEQUENCE: 68

Leu Asp Lys Tyr Gln Asn Ile Tyr
1               5

<210> SEQ ID NO 69
<211> LENGTH: 8
<212> TYPE: PRT
<213> ORGANISM: Enterococcus faecium

<400> SEQUENCE: 69
```

```
Lys Val Trp Val Ile Gly Val Asp
1               5

<210> SEQ ID NO 70
<211> LENGTH: 19
<212> TYPE: PRT
<213> ORGANISM: Enterococcus faecium

<400> SEQUENCE: 70

Asn Phe Val Ile Ile Asp Asp Val Ile Asp Gly Leu Asp Asn Val Val
1               5                   10                  15

Ser Ala Thr

<210> SEQ ID NO 71
<211> LENGTH: 14
<212> TYPE: PRT
<213> ORGANISM: Enterococcus faecium

<400> SEQUENCE: 71

Thr Ser Thr Leu Lys Ala Val Gly Thr Val Val Glu Asp Leu
1               5                   10

<210> SEQ ID NO 72
<211> LENGTH: 10
<212> TYPE: PRT
<213> ORGANISM: Enterococcus faecium

<400> SEQUENCE: 72

Ser Tyr Leu Ala Gly Val Ala Ala Ala Tyr
1               5                   10

<210> SEQ ID NO 73
<211> LENGTH: 8
<212> TYPE: PRT
<213> ORGANISM: Enterococcus faecium

<400> SEQUENCE: 73

Glu Ile Lys Val Leu Asn Gln Tyr
1               5

<210> SEQ ID NO 74
<211> LENGTH: 9
<212> TYPE: PRT
<213> ORGANISM: Enterococcus faecium

<400> SEQUENCE: 74

Thr Asn Val Val Gly Phe Ile Gly Gly
1               5

<210> SEQ ID NO 75
<211> LENGTH: 7
<212> TYPE: PRT
<213> ORGANISM: Enterococcus faecium

<400> SEQUENCE: 75

Glu His Thr Val Tyr Gly Leu
1               5

<210> SEQ ID NO 76
<211> LENGTH: 8
<212> TYPE: PRT
<213> ORGANISM: Enterococcus faecium

<400> SEQUENCE: 76
```

Ser Gly Asp Val Lys Val Pro Glu
1               5

<210> SEQ ID NO 77
<211> LENGTH: 12
<212> TYPE: PRT
<213> ORGANISM: Enterococcus faecium

<400> SEQUENCE: 77

Gly Ile Gly Tyr Lys Leu Lys Pro Ala Ile Gln Glu
1               5                   10

<210> SEQ ID NO 78
<211> LENGTH: 8
<212> TYPE: PRT
<213> ORGANISM: Enterococcus faecium

<400> SEQUENCE: 78

Asn Ala Asp Ile Ile Phe His Ala
1               5

<210> SEQ ID NO 79
<211> LENGTH: 7
<212> TYPE: PRT
<213> ORGANISM: Enterococcus faecium

<400> SEQUENCE: 79

Lys Ala Gly Val Asp Ala Gly
1               5

<210> SEQ ID NO 80
<211> LENGTH: 9
<212> TYPE: PRT
<213> ORGANISM: Enterococcus faecium

<400> SEQUENCE: 80

Glu Asp Gly Val Gly Leu Thr Glu Gly
1               5

<210> SEQ ID NO 81
<211> LENGTH: 6
<212> TYPE: PRT
<213> ORGANISM: Enterococcus faecium

<400> SEQUENCE: 81

Lys Lys Ala Val Asp Glu
1               5

<210> SEQ ID NO 82
<211> LENGTH: 24
<212> TYPE: PRT
<213> ORGANISM: Enterococcus faecium

<400> SEQUENCE: 82

Glu His Thr Tyr Val Ala Pro Val Glu Thr Val Glu Val Ala Pro Ala
1               5                   10                  15

Ala Pro Ala Ala Ala Thr Ala Pro
            20

<210> SEQ ID NO 83
<211> LENGTH: 9
<212> TYPE: PRT
<213> ORGANISM: Enterococcus faecium

<400> SEQUENCE: 83

Val Ala Glu Gln Tyr Val Thr Ser Arg
1               5

<210> SEQ ID NO 84
<211> LENGTH: 11
<212> TYPE: PRT
<213> ORGANISM: Enterococcus faecium

<400> SEQUENCE: 84

Arg Ile Tyr Val Gly Glu Gln Leu Thr Ile Pro
1               5                   10

<210> SEQ ID NO 85
<211> LENGTH: 13
<212> TYPE: PRT
<213> ORGANISM: Enterococcus faecium

<400> SEQUENCE: 85

Gly Arg Tyr Gln Leu Asp Ala Ser Tyr Leu Asn Gly Asp
1               5                   10

<210> SEQ ID NO 86
<211> LENGTH: 7
<212> TYPE: PRT
<213> ORGANISM: Enterococcus faecium

<400> SEQUENCE: 86

Leu Ser Lys Ile Ser Gln Lys
1               5

<210> SEQ ID NO 87
<211> LENGTH: 16
<212> TYPE: PRT
<213> ORGANISM: Enterococcus faecium

<400> SEQUENCE: 87

Ser Thr Val Pro Val Val Leu Lys Ser Pro Val Lys Val Trp Val Arg
1               5                   10                  15

<210> SEQ ID NO 88
<211> LENGTH: 15
<212> TYPE: PRT
<213> ORGANISM: Enterococcus faecium

<400> SEQUENCE: 88

Ser Ile Thr Lys Ile Ile Gly Leu Tyr Ile Val Leu Asp Gln Val
1               5                   10                  15

<210> SEQ ID NO 89
<211> LENGTH: 8
<212> TYPE: PRT
<213> ORGANISM: Enterococcus faecium

<400> SEQUENCE: 89

Ala Gly Ala Cys Phe Val Gly Thr
1               5

<210> SEQ ID NO 90
<211> LENGTH: 8
<212> TYPE: PRT
<213> ORGANISM: Enterococcus faecium

<400> SEQUENCE: 90

Ile Ile Thr Val Val Leu Asn Ala

```
-continued
```

```
<210> SEQ ID NO 91
<211> LENGTH: 24
<212> TYPE: PRT
<213> ORGANISM: Enterococcus faecium

<400> SEQUENCE: 91

Ala Gln Asp Val Ala Ile Val Ala Arg His Leu Ile Leu Asp Phe Pro
1               5                   10                  15

Glu Ile Leu Asp Val Ser Ser Thr
            20

<210> SEQ ID NO 92
<211> LENGTH: 14
<212> TYPE: PRT
<213> ORGANISM: Enterococcus faecium

<400> SEQUENCE: 92

Asn Leu Ser Val Thr Pro Asp Leu Ser Asn Val Pro Leu His
1               5                   10

<210> SEQ ID NO 93
<211> LENGTH: 9
<212> TYPE: PRT
<213> ORGANISM: Enterococcus faecium

<400> SEQUENCE: 93

Ala Ser Met Val Ala Leu Ala Glu Lys
1               5

<210> SEQ ID NO 94
<211> LENGTH: 13
<212> TYPE: PRT
<213> ORGANISM: Enterococcus faecium

<400> SEQUENCE: 94

Lys Val Asn Ala Lys Ala Ala Phe Ala Val Asp Ala Gln
1               5                   10

<210> SEQ ID NO 95
<211> LENGTH: 6
<212> TYPE: PRT
<213> ORGANISM: Enterococcus faecium

<400> SEQUENCE: 95

Lys Val Ser Ile Ser Asp
1               5

<210> SEQ ID NO 96
<211> LENGTH: 7
<212> TYPE: PRT
<213> ORGANISM: Enterococcus faecium

<400> SEQUENCE: 96

Pro Gly Phe Val Asn Tyr Lys
1               5

<210> SEQ ID NO 97
<211> LENGTH: 13
<212> TYPE: PRT
<213> ORGANISM: Enterococcus faecium

<400> SEQUENCE: 97
```

```
Val Lys Glu Leu Phe Asp Ser Ala Ile Ile Gln Ser Ala
1               5                   10
```

<210> SEQ ID NO 98
<211> LENGTH: 6
<212> TYPE: PRT
<213> ORGANISM: Enterococcus faecium

<400> SEQUENCE: 98

```
Met Asp Tyr Cys Tyr Asp
1               5
```

<210> SEQ ID NO 99
<211> LENGTH: 10
<212> TYPE: PRT
<213> ORGANISM: Enterococcus faecium

<400> SEQUENCE: 99

```
Lys Ala Asn Ile Phe Val Ile Gly Trp Arg
1               5                   10
```

<210> SEQ ID NO 100
<211> LENGTH: 6
<212> TYPE: PRT
<213> ORGANISM: Enterococcus faecium

<400> SEQUENCE: 100

```
Gln Ser Pro Val Glu Met
1               5
```

<210> SEQ ID NO 101
<211> LENGTH: 7
<212> TYPE: PRT
<213> ORGANISM: Enterococcus faecium

<400> SEQUENCE: 101

```
Ala Thr Ile Val Asn Ala Ser
1               5
```

<210> SEQ ID NO 102
<211> LENGTH: 10
<212> TYPE: PRT
<213> ORGANISM: Enterococcus faecium

<400> SEQUENCE: 102

```
Ala Ser Ile Pro Ser Leu Lys Thr Ile Asp
1               5                   10
```

<210> SEQ ID NO 103
<211> LENGTH: 6
<212> TYPE: PRT
<213> ORGANISM: Enterococcus faecium

<400> SEQUENCE: 103

```
Gly Lys Ile Leu Tyr Asp
1               5
```

<210> SEQ ID NO 104
<211> LENGTH: 7
<212> TYPE: PRT
<213> ORGANISM: Enterococcus faecium

<400> SEQUENCE: 104

```
Thr Ile Thr Leu Ala Glu Asp
1               5
```

```
<210> SEQ ID NO 105
<211> LENGTH: 11
<212> TYPE: PRT
<213> ORGANISM: Enterococcus faecium

<400> SEQUENCE: 105

Tyr Ala Thr Glu Tyr Tyr Val Val Lys Met Val
1               5                   10

<210> SEQ ID NO 106
<211> LENGTH: 11
<212> TYPE: PRT
<213> ORGANISM: Enterococcus faecium

<400> SEQUENCE: 106

Phe Glu Ala Gly Leu Lys Ala His Val Asp Ile
1               5                   10

<210> SEQ ID NO 107
<211> LENGTH: 15
<212> TYPE: PRT
<213> ORGANISM: Enterococcus faecium

<400> SEQUENCE: 107

Gln Ser Leu Val Gln Arg Met Ile Ile Tyr Lys Val Phe Asn Asn
1               5                   10                  15

<210> SEQ ID NO 108
<211> LENGTH: 7
<212> TYPE: PRT
<213> ORGANISM: Enterococcus faecium

<400> SEQUENCE: 108

Glu Asn Val Leu Ser Ala Phe
1               5

<210> SEQ ID NO 109
<211> LENGTH: 15
<212> TYPE: PRT
<213> ORGANISM: Enterococcus faecium

<400> SEQUENCE: 109

Lys Ser Phe His Pro Glu Val Glu Ala Gln Ile Ile Lys Leu Ser
1               5                   10                  15

<210> SEQ ID NO 110
<211> LENGTH: 7
<212> TYPE: PRT
<213> ORGANISM: Enterococcus faecium

<400> SEQUENCE: 110

Thr Ile Thr Val Ser Asp Phe
1               5

<210> SEQ ID NO 111
<211> LENGTH: 7
<212> TYPE: PRT
<213> ORGANISM: Enterococcus faecium

<400> SEQUENCE: 111

Thr Thr Lys Val Ile Gly Glu
1               5
```

```
<210> SEQ ID NO 112
<211> LENGTH: 7
<212> TYPE: PRT
<213> ORGANISM: Enterococcus faecium

<400> SEQUENCE: 112

Asp Lys Gln Val Asp Ala Glu
1               5

<210> SEQ ID NO 113
<211> LENGTH: 11
<212> TYPE: PRT
<213> ORGANISM: Enterococcus faecium

<400> SEQUENCE: 113

Pro Ala Glu Val Lys Glu Ala Ala Phe Lys Leu
1               5                   10

<210> SEQ ID NO 114
<211> LENGTH: 7
<212> TYPE: PRT
<213> ORGANISM: Enterococcus faecium

<400> SEQUENCE: 114

Glu Ser Gln Leu Glu Ala Ala
1               5

<210> SEQ ID NO 115
<211> LENGTH: 7
<212> TYPE: PRT
<213> ORGANISM: Enterococcus faecium

<400> SEQUENCE: 115

Lys Asp Gln Leu Lys Asp Ile
1               5

<210> SEQ ID NO 116
<211> LENGTH: 6
<212> TYPE: PRT
<213> ORGANISM: Enterococcus faecium

<400> SEQUENCE: 116

Ser Lys Leu Ala Lys Asp
1               5

<210> SEQ ID NO 117
<211> LENGTH: 28
<212> TYPE: PRT
<213> ORGANISM: Enterococcus faecium

<400> SEQUENCE: 117

Ala Asn Ala Ile Leu Gly Val Ser Ile Ala Val Ala Arg Ala Ala Ala
1               5                   10                  15

Asp Tyr Leu Glu Val Pro Leu Tyr His Tyr Leu Gly
            20                  25

<210> SEQ ID NO 118
<211> LENGTH: 7
<212> TYPE: PRT
<213> ORGANISM: Enterococcus faecium

<400> SEQUENCE: 118

Gly Val Tyr Val Leu Ala Asp
1               5
```

<210> SEQ ID NO 119
<211> LENGTH: 8
<212> TYPE: PRT
<213> ORGANISM: Enterococcus faecium

<400> SEQUENCE: 119

Tyr Thr Ala Val Val Ser His Arg
1               5

<210> SEQ ID NO 120
<211> LENGTH: 13
<212> TYPE: PRT
<213> ORGANISM: Enterococcus faecium

<400> SEQUENCE: 120

Glu Val Phe His Ala Leu Ala Ser Ile Leu Lys Ala Arg
1               5                   10

<210> SEQ ID NO 121
<211> LENGTH: 14
<212> TYPE: PRT
<213> ORGANISM: Enterococcus faecium

<400> SEQUENCE: 121

Tyr Glu Glu Leu Val Ser Lys Tyr Pro Ile Ile Ser Ile Glu
1               5                   10

<210> SEQ ID NO 122
<211> LENGTH: 15
<212> TYPE: PRT
<213> ORGANISM: Enterococcus faecium

<400> SEQUENCE: 122

Lys Ala Gly Tyr Val Pro Gly Lys Asp Val Val Leu Ala Met Asp
1               5                   10                  15

<210> SEQ ID NO 123
<211> LENGTH: 9
<212> TYPE: PRT
<213> ORGANISM: Enterococcus faecium

<400> SEQUENCE: 123

Ile Thr Asp Val Tyr Ala Arg Glu Ile
1               5

<210> SEQ ID NO 124
<211> LENGTH: 21
<212> TYPE: PRT
<213> ORGANISM: Enterococcus faecium

<400> SEQUENCE: 124

Leu Thr Asp Val Leu Gly Asp Lys Val Gln Leu Val Gly Asp Asp Leu
1               5                   10                  15

Phe Val Thr Asn Thr
            20

<210> SEQ ID NO 125
<211> LENGTH: 8
<212> TYPE: PRT
<213> ORGANISM: Enterococcus faecium

<400> SEQUENCE: 125

Ser Asp Ile Ala Val Ala Thr Asn
1               5

<210> SEQ ID NO 126
<211> LENGTH: 7
<212> TYPE: PRT
<213> ORGANISM: Enterococcus faecium

<400> SEQUENCE: 126

Glu Val Glu Val Tyr Thr Glu
1               5

<210> SEQ ID NO 127
<211> LENGTH: 10
<212> TYPE: PRT
<213> ORGANISM: Enterococcus faecium

<400> SEQUENCE: 127

Asn Ser Ile Leu Ile Lys Val Asn Gln Ile
1               5                   10

<210> SEQ ID NO 128
<211> LENGTH: 9
<212> TYPE: PRT
<213> ORGANISM: Enterococcus faecium

<400> SEQUENCE: 128

Ala Glu Ala Ile Ile Gly Tyr Asp Val
1               5

<210> SEQ ID NO 129
<211> LENGTH: 8
<212> TYPE: PRT
<213> ORGANISM: Enterococcus faecium

<400> SEQUENCE: 129

Phe Glu Val Ile Ile Glu Ala Ile
1               5

<210> SEQ ID NO 130
<211> LENGTH: 14
<212> TYPE: PRT
<213> ORGANISM: Enterococcus faecium

<400> SEQUENCE: 130

Leu Gly Glu Val Ala Glu Tyr Lys Gly Leu Lys Ser Phe Tyr
1               5                   10

<210> SEQ ID NO 131
<211> LENGTH: 6
<212> TYPE: PRT
<213> ORGANISM: Enterococcus faecium

<400> SEQUENCE: 131

Thr Lys Val Leu Pro Thr
1               5

<210> SEQ ID NO 132
<211> LENGTH: 8
<212> TYPE: PRT
<213> ORGANISM: Enterococcus faecium

<400> SEQUENCE: 132

Tyr Asn Gln Leu Leu Arg Ile Glu
1               5

<210> SEQ ID NO 133
<211> LENGTH: 7
<212> TYPE: PRT
<213> ORGANISM: Enterococcus faecium

<400> SEQUENCE: 133

Thr Lys Ala Val Asp Asn Val
1               5

<210> SEQ ID NO 134
<211> LENGTH: 7
<212> TYPE: PRT
<213> ORGANISM: Enterococcus faecium

<400> SEQUENCE: 134

Ile Met Pro Val Gly Ala Pro
1               5

<210> SEQ ID NO 135
<211> LENGTH: 6
<212> TYPE: PRT
<213> ORGANISM: Enterococcus faecium

<400> SEQUENCE: 135

Tyr Glu Ala Val Glu Leu
1               5

<210> SEQ ID NO 136
<211> LENGTH: 11
<212> TYPE: PRT
<213> ORGANISM: Enterococcus faecium

<400> SEQUENCE: 136

Gly Gly His Leu Val Tyr Arg Leu Tyr Asn Lys
1               5                   10

<210> SEQ ID NO 137
<211> LENGTH: 13
<212> TYPE: PRT
<213> ORGANISM: Enterococcus faecium

<400> SEQUENCE: 137

Tyr Asn Gln Val His Gln Ile Asn Leu Leu Cys Asn Asn
1               5                   10

<210> SEQ ID NO 138
<211> LENGTH: 12
<212> TYPE: PRT
<213> ORGANISM: Enterococcus faecium

<400> SEQUENCE: 138

Gln Asp Leu Leu Glu Ser Leu Gly Cys Tyr Gly Ala
1               5                   10

<210> SEQ ID NO 139
<211> LENGTH: 10
<212> TYPE: PRT
<213> ORGANISM: Enterococcus faecium

<400> SEQUENCE: 139

Lys Glu Leu Gln Val Ser Phe Ser His Tyr
1               5                   10

<210> SEQ ID NO 140
<211> LENGTH: 13

```
<212> TYPE: PRT
<213> ORGANISM: Enterococcus faecium

<400> SEQUENCE: 140

Ile Leu Gly Leu Gly His Asn Phe Val Val Asp Ser Ala
1               5                   10

<210> SEQ ID NO 141
<211> LENGTH: 7
<212> TYPE: PRT
<213> ORGANISM: Enterococcus faecium

<400> SEQUENCE: 141

Lys Pro Lys Val Asn Lys Ser
1               5

<210> SEQ ID NO 142
<211> LENGTH: 19
<212> TYPE: PRT
<213> ORGANISM: Enterococcus faecium

<400> SEQUENCE: 142

Gly Asp Ser Val Thr Leu Thr Ala Pro Ser Ile Gln Gly Tyr Val Leu
1               5                   10                  15

Asp Asp Arg

<210> SEQ ID NO 143
<211> LENGTH: 18
<212> TYPE: PRT
<213> ORGANISM: Enterococcus faecium

<400> SEQUENCE: 143

Ile Tyr Arg Leu Phe Leu Pro Gly Val Lys Ser Gly Ser His His Tyr
1               5                   10                  15

Thr Ala

<210> SEQ ID NO 144
<211> LENGTH: 8
<212> TYPE: PRT
<213> ORGANISM: Enterococcus faecium

<400> SEQUENCE: 144

Thr Gly Leu Tyr Ile Asp Asp Leu
1               5

<210> SEQ ID NO 145
<211> LENGTH: 12
<212> TYPE: PRT
<213> ORGANISM: Enterococcus faecium

<400> SEQUENCE: 145

Val Asn Ile Leu Lys Glu Gln Ile Val Asn Val Thr
1               5                   10

<210> SEQ ID NO 146
<211> LENGTH: 7
<212> TYPE: PRT
<213> ORGANISM: Enterococcus faecium

<400> SEQUENCE: 146

Asn Val Thr Val Asn His Val
1               5
```

<210> SEQ ID NO 147
<211> LENGTH: 8
<212> TYPE: PRT
<213> ORGANISM: Enterococcus faecium

<400> SEQUENCE: 147

Leu Glu Ala Leu Tyr Thr Ser Val
1               5

<210> SEQ ID NO 148
<211> LENGTH: 10
<212> TYPE: PRT
<213> ORGANISM: Enterococcus faecium

<400> SEQUENCE: 148

Val Asp Asn Val Phe Ile Ser Ala Asn Pro
1               5                   10

<210> SEQ ID NO 149
<211> LENGTH: 7
<212> TYPE: PRT
<213> ORGANISM: Enterococcus faecium

<400> SEQUENCE: 149

Lys Lys Pro Val Pro Thr Val
1               5

<210> SEQ ID NO 150
<211> LENGTH: 8
<212> TYPE: PRT
<213> ORGANISM: Enterococcus faecium

<400> SEQUENCE: 150

Leu Gln Ala Leu Tyr Asn Arg Val
1               5

<210> SEQ ID NO 151
<211> LENGTH: 6
<212> TYPE: PRT
<213> ORGANISM: Enterococcus faecium

<400> SEQUENCE: 151

Asp His Leu Val Lys Ile
1               5

<210> SEQ ID NO 152
<211> LENGTH: 6
<212> TYPE: PRT
<213> ORGANISM: Enterococcus faecium

<400> SEQUENCE: 152

Asn Ala Val Leu Ser Ser
1               5

<210> SEQ ID NO 153
<211> LENGTH: 7
<212> TYPE: PRT
<213> ORGANISM: Enterococcus faecium

<400> SEQUENCE: 153

Asn Tyr Phe Leu Cys Arg Asn
1               5

<210> SEQ ID NO 154
<211> LENGTH: 10

```
<212> TYPE: PRT
<213> ORGANISM: Enterococcus faecium

<400> SEQUENCE: 154

Asn Asp Ile Val Gln Gln Ala Ala Asp Ile
1               5                   10

<210> SEQ ID NO 155
<211> LENGTH: 6
<212> TYPE: PRT
<213> ORGANISM: Enterococcus faecium

<400> SEQUENCE: 155

Ser Gln Ala Gln Val Asn
1               5

<210> SEQ ID NO 156
<211> LENGTH: 14
<212> TYPE: PRT
<213> ORGANISM: Enterococcus faecium

<400> SEQUENCE: 156

Gly Gln Val Ile Ala Thr Asp Gln Ala Lys Val Thr Ser Gly
1               5                   10

<210> SEQ ID NO 157
<211> LENGTH: 7
<212> TYPE: PRT
<213> ORGANISM: Enterococcus faecium

<400> SEQUENCE: 157

Glu Tyr Thr Val Thr Ile Asn
1               5

<210> SEQ ID NO 158
<211> LENGTH: 9
<212> TYPE: PRT
<213> ORGANISM: Enterococcus faecium

<400> SEQUENCE: 158

Asn Ala Asn Leu Leu Tyr Asn Asn Gln
1               5

<210> SEQ ID NO 159
<211> LENGTH: 13
<212> TYPE: PRT
<213> ORGANISM: Enterococcus faecium

<400> SEQUENCE: 159

Thr Ala Leu Ser Asn Ala Lys Lys Val Leu Asp Asp Ser
1               5                   10

<210> SEQ ID NO 160
<211> LENGTH: 7
<212> TYPE: PRT
<213> ORGANISM: Enterococcus faecium

<400> SEQUENCE: 160

Thr Phe Lys Tyr Lys Lys Ile
1               5

<210> SEQ ID NO 161
<211> LENGTH: 10
<212> TYPE: PRT
<213> ORGANISM: Enterococcus faecium
```

```
<400> SEQUENCE: 161

Asp Ala Ala Phe Lys Gly Leu Gln His Lys
1               5                   10

<210> SEQ ID NO 162
<211> LENGTH: 7
<212> TYPE: PRT
<213> ORGANISM: Enterococcus faecium

<400> SEQUENCE: 162

Gln Asn Gly Val Ala Pro Met
1               5

<210> SEQ ID NO 163
<211> LENGTH: 6
<212> TYPE: PRT
<213> ORGANISM: Enterococcus faecium

<400> SEQUENCE: 163

Gln Lys Gln Val Asp Ser
1               5

<210> SEQ ID NO 164
<211> LENGTH: 7
<212> TYPE: PRT
<213> ORGANISM: Enterococcus faecium

<400> SEQUENCE: 164

Ala Lys Lys Val Leu Asn Asp
1               5

<210> SEQ ID NO 165
<211> LENGTH: 7
<212> TYPE: PRT
<213> ORGANISM: Enterococcus faecium

<400> SEQUENCE: 165

Arg Asp His His Tyr Thr Ala
1               5

<210> SEQ ID NO 166
<211> LENGTH: 6
<212> TYPE: PRT
<213> ORGANISM: Enterococcus faecium

<400> SEQUENCE: 166

Lys Ala Lys Ala Phe Lys
1               5

<210> SEQ ID NO 167
<211> LENGTH: 7
<212> TYPE: PRT
<213> ORGANISM: Enterococcus faecium

<400> SEQUENCE: 167

Asp Ser Ala Tyr Lys Gly Leu
1               5
```